United States Patent
Brusa et al.

(10) Patent No.: US 11,866,793 B2
(45) Date of Patent: Jan. 9, 2024

(54) ASSAY FOR DETECTING PALMER AMARANTH DNA IN INDIVIDUAL AND MIXED SAMPLES

(71) Applicant: REGENTS OF THE UNIVERSITY OF MINNESOTA, Minneapolis, MN (US)

(72) Inventors: Anthony Brusa, Minneapolis, MN (US); Kevin Dorn, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 308 days.

(21) Appl. No.: 17/214,248

(22) Filed: Mar. 26, 2021

(65) Prior Publication Data

US 2021/0301355 A1 Sep. 30, 2021

Related U.S. Application Data

(60) Provisional application No. 63/000,946, filed on Mar. 27, 2020.

(51) Int. Cl.
*C12Q 1/68* (2018.01)
*C12Q 1/6895* (2018.01)

(52) U.S. Cl.
CPC ....... *C12Q 1/6895* (2013.01); *C12Q 2600/13* (2013.01)

(58) Field of Classification Search
None
See application file for complete search history.

(56) References Cited

U.S. PATENT DOCUMENTS

| 8,455,190 B2 | 6/2013 | Makrigiorgos |
| 9,963,750 B2 | 5/2018 | Kessler |

FOREIGN PATENT DOCUMENTS

| CN | 104561314 A | 4/2015 |
| CN | 105400869 A | 3/2016 |
| WO | 2017196720 A1 | 11/2017 |

OTHER PUBLICATIONS

Brusa et al. Pest Manag Sci 2021; 77: 2477-2484 (Year: 2021).*
LGC genomics. KASP genotyping. 2014. www.lgcgenomics.com. pp. 1-3 (Year: 2014).*
Berger, S., et al., 2016. Palmer amaranth (Amaranthus palmeri) identification and documentation of ALS-resistance in Argentina. Weed Science 64, 312-320.
Culpepper, A.S., et al. 2006. Glyphosate-resistant Palmer amaranth (Amaranthus palmeri) confirmed in Georgia. Weed Science 54, 620-626.
Ertiro, B.T., et al., 2015. Comparison of Kompetitive Allele Specific PCR (KASP) and genotyping by sequencing (GBS) for quality control analysis in maize. BMC Genomics 16, 1-12.
Gaines, T.A., et al., 2012. Interspecific hybridization transfers a previously unknown glyphosate resistance mechanism in *Amaranthus* species. Evol. Appl. 5, 29-38.
Gaines, T.A., et al., 2010. Gene amplification confers glyphosate resistance in Amaranthus palmeri. Proc. Natl. Acad. Sci. 107, 1029-1034.
Garrison, E., et al., 2012. Haplotype-based variant detection from short-read sequencing. arXiv preprint arXiv:1207.3907, pp. 1-8.
Heap, I. The International Survey of Herbicide Resistant Weeds. Online. Internet. Monday, Nov. 25, 2019. Accessed online at http://web.archive.org/web/20220428162246/https://www.mssoy.org/uploads/files/pp-graphs-heap-2019.pdf, 21 pages.
Jhala, A.J., et al., 2014. Confirmation and Control of Triazine and 4-Hydroxyphenylpyruvate Dioxygenase-Inhibiting Herbicide-Resistant Palmer Amaranth ( Amaranthus palmeri ) in Nebraska . Weed Technol. 28, 28-38.
Klingaman, T., et al., 1994. Palmer Amaranth (Amaranthus palmeri) Interference in Soybeans (*Glycine max*). Weed Sci. 42, 523-527.
Kohrt, J.R., et al., 2017. Herbicide Management Strategies in Field Corn for a Three-Way Herbicide-Resistant Palmer Amaranth (Amaranthuspalmeri) Population. Weed Technol. 31, 364-372.
Kohrt, J.R., et al., 2017. Confirmation of a three-way (glyphosate, als, and atrazine)herbicide-resistant population of palmer amaranth (amaranthus palmeri) in Michigan. Weed Sci. 65, 327-338.
Küpper, A., et al, 2017. Multiple resistance to glyphosate and acetolactate synthase inhibitors in palmer amaranth (amaranthus palmeri) identified in Brazil. Weed Sci. 65, 317-326.
Massinga, R.A., et al., 2001. Interference of Palmer Amaranth in Corn. Weed Sci. 49, 202-208.
Minnesota Department of Agriculture, 2020. Palmer Amaranth in Minnesota [WWW Document]. Date accessed Jun. 1, 2020. Available online at http://web.archive.org/web/20200601234716/https://www.mda.state.mn.us/plants-insects/palmer-amaranth-minnesota, 3 pages.
Molin, W.T., et al., 2016. Transfer and Expression of ALS Inhibitor Resistance from Palmer Amaranth (Amaranthus palmeri) to an A. spinosus x A. palmeri Hybrid . Weed Sci. 64, 240-247.
Morgan, G.D., et al. 2001. Competitive Impact of Palmer Amaranth (Amaranthus palmeri) on Cotton (*Gossypium hirsutum*) Development and Yield. Weed Technol. 15, 408-412.
Murphy, B.P., et al., 2017. A quantitative assay for Amaranthus palmeri identification. Pest Manag. Sci. 73, 2221-2224.
Nakka, S., et al., 2017. Rapid detoxification via glutathione S-transferase (GST) conjugation confers a high level of atrazine resistance in Palmer amaranth (Amaranthus palmeri). Pest Manag. Sci. 73, 2236-2243.
Nakka, S., et al., 2017. Target Site-Based and Non-Target Site Based Resistance to ALS Inhibitors in Palmer Amaranth (Amaranthus palmeri). Weed Sci. 65, 681-689.
Nandula, V.K., et al., 2012. Multiple Resistance to Glyphosateand Pyrithiobacin Palmer Amaranth (Amaranthuspalmeri) from Mississippi and Response to Flumiclorac. Weed Sci. 60, 179-188.

(Continued)

*Primary Examiner* — Juliet C Switzer
(74) *Attorney, Agent, or Firm* — QUARLES & BRADY LLP

(57) ABSTRACT

The present invention provides methods and kits for identifying *Amaranthus palmeri* plant material using genetic markers. The methods may be used to determine whether a sample contains *Amaranthus palmeri* plant material or to genotype an *Amaranthus* plant.

18 Claims, 4 Drawing Sheets

Specification includes a Sequence Listing.

(56) References Cited

OTHER PUBLICATIONS

Nandula, V.K., et al., 2014. EPSPS amplification in glyphosate-resistant spiny amaranth (Amaranthus spinosus): A case of gene transfer via interspecific hybridization from glyphosate-resistant Palmer amaranth (Amaranthus palmeri). Pest Manag. Sci. 70, 1902-1909.

Oliveira, M.C., et al., 2018. Interspecific and intraspecific transference of metabolism-based mesotrione resistance in dioecious weedy Amaranthus. Plant Journal 96, 1051-1063.

Patterson, E.L., et al., 2017. A KASP genotyping method to identify northern watermilfoil, Eurasian watermilfoil, and their interspecific hybrids. Front. Plant Sci. 8, 1-10.

Patterson, E.L., et al., 2019. Omics Potential in Herbicide-Resistant Weed Management. Plants 8, 1-14.

Patzoldt W.L., et al., 2006. A codon deletion confers resistance to herbicides inhibiting protoporphyrinogen oxidase. Proc Natl Acad Sci USA 103, 12329-12334.

Ravet, K., et al., 2018. The power and potential of genomics in weed biology and management. Pest Manag. Sci. 74, 2216-2225.

Saiki, R.K., et al., 1985. Enzymatic amplification of β-globin genomic sequences and restriction site analysis for diagnosis of sickle cell anemia. Science 230, 1350-1354.

Salas, R.A., et al., 2016. Resistance to PPO-inhibiting herbicide in Palmer amaranth from Arkansas. Pest Manag. Sci. 72, 864-869.

Salas-Perez, R.A., et al., 2017. Frequency of Gly-210 Deletion Mutation among Protoporphyrinogen Oxidase Inhibitor-Resistant Palmer Amaranth (Amaranthus palmeri) Populations. Weed Sci. 65, 718-731.

Schwartz-Lazaro, L.M., et al., 2017. Resistance of two Arkansas Palmer amaranth populations to multiple herbicide sites of action. Crop Prot. 96, 158-163.

Semagn et al., 2013. Single nucleotide polymorphism genotyping using Kompetitive Allele Specific PCR (KASP): overview of the technology and its application in crop improvement. Molecular Breeding 33, 1-14.

Sosnoskie, L.M., et al., 2011. Multiple Resistance in Palmer Amaranth to Glyphosate and Pyrithiobac Confirmed in Georgia. Weed Sci. 59, 321-325.

Sosnoskie, L.M., et al., 2012. Pollen-Mediated Dispersal of Glyphosate-Resistance in Palmer Amaranth under Field Conditions. Weed Sci. 60, 366-373.

Trucco, F., et al., 2005. Amaranthus hybridus can be pollinated frequently by A. tuberculatus under field conditions. Heredity 94, 64-70.

Trucco, F., et al., 2009. Out of the swamp: Unidirectional hybridization with weedy species may explain the prevalence of Amaranthus tuberculatus as a weed. New Phytologist 184, 819-827.

Varanasi, V.K., et al., 2018. Confirmation and Characterization of Non-target site Resistance to Fomesafen in Palmer amaranth (Amaranthuspalmeri). Weed Sci. 66, 702-709.

Ward, S.M., et al., 2013. Palmer Amaranth (Amaranthus palmeri): A Review. Weed Technol. 27, 12-27.

Wetzel, D. K., et al., 1999. Use of PCR-based molecular markers to identify weedy *Amaranthus* species. Weed Science 47, 518-523.

Wright, A. A., et al., 2016. Distinguishing between weedy *Amaranthus* species based on intron 1 sequences from the 5-enolpyruvylshikimate-3-phosphate synthase gene. Pest Manag Sci 72, 2347-2354.

Yuan, J., et al., 2014. Introduction of high throughput and cost effective SNP genotyping platforms in soybean. Plant Genetics, Genomics and Biotechnology 2, 90-94.

\* cited by examiner

SEQUENCE LISTING

```
<160> NUMBER OF SEQ ID NOS: 19

<210> SEQ ID NO 1
<211> LENGTH: 17
<212> TYPE: DNA
<213> ORGANISM: Artificial Sequence
<220> FEATURE:
<223> OTHER INFORMATION: Synthetic - Minimum primer for detection of A.
      palmeri allele at Marker 2

<400> SEQUENCE: 1
```

```
gaaaaagtgt ttagagt                                                   17

<210> SEQ ID NO 2
<211> LENGTH: 17
<212> TYPE: DNA
<213> ORGANISM: Artificial Sequence
<220> FEATURE:
<223> OTHER INFORMATION: Synthetic - Minimum primer for detection of
      non-A. palmeri allele at Marker 2

<400> SEQUENCE: 2
gaaaaagtgt ttagagg                                                   17

<210> SEQ ID NO 3
<211> LENGTH: 15
<212> TYPE: DNA
<213> ORGANISM: Artificial Sequence
<220> FEATURE:
<223> OTHER INFORMATION: Synthetic - Minimum reverse primer for
      detection of Marker 2

<400> SEQUENCE: 3
caaaatctgc ctaca                                                     15

<210> SEQ ID NO 4
<211> LENGTH: 13
<212> TYPE: DNA
<213> ORGANISM: Artificial Sequence
<220> FEATURE:
<223> OTHER INFORMATION: Synthetic - Minimum primer for detection of A.
      palmeri allele at Marker 3

<400> SEQUENCE: 4
gttaggaaag cgt                                                       13

<210> SEQ ID NO 5
<211> LENGTH: 13
<212> TYPE: DNA
<213> ORGANISM: Artificial Sequence
<220> FEATURE:
<223> OTHER INFORMATION: Synthetic - Minimum primer for detection of
      non-A. palmeri allele at Marker 3

<400> SEQUENCE: 5
gttaggaaag cgg                                                       13

<210> SEQ ID NO 6
<211> LENGTH: 15
<212> TYPE: DNA
<213> ORGANISM: Artificial Sequence
<220> FEATURE:
<223> OTHER INFORMATION: Synthetic - Minimum reverse primer for
      detection of Marker 3

<400> SEQUENCE: 6
gacttgatga gcttt                                                     15

<210> SEQ ID NO 7
<211> LENGTH: 22
<212> TYPE: DNA
<213> ORGANISM: Artificial Sequence
<220> FEATURE:
<223> OTHER INFORMATION: Synthetic - Minimum primer for detection of A.
      palmeri allele at Marker 1

<400> SEQUENCE: 7
```
cgggcgtgga tggcctaaaa ag                                          22

<210> SEQ ID NO 8
<211> LENGTH: 22
<212> TYPE: DNA
<213> ORGANISM: Artificial Sequence
<220> FEATURE:
<223> OTHER INFORMATION: Synthetic - Minimum primer for detection of
      non-A. palmeri allele at Marker 1

<400> SEQUENCE: 8
cgggcgtgga tggcctaaaa ca                                          22

<210> SEQ ID NO 9
<211> LENGTH: 18
<212> TYPE: DNA
<213> ORGANISM: Artificial Sequence
<220> FEATURE:
<223> OTHER INFORMATION: Synthetic - Minimum reverse primer for
      detection of Marker 1

<400> SEQUENCE: 9
accaatcgcc gcagcagc                                               18

<210> SEQ ID NO 10
<211> LENGTH: 21
<212> TYPE: DNA
<213> ORGANISM: Artificial Sequence
<220> FEATURE:
<223> OTHER INFORMATION: Synthetic - Sequence of FAM tail

<400> SEQUENCE: 10
gaaggtcgga gtcaacggat t                                           21

<210> SEQ ID NO 11
<211> LENGTH: 21
<212> TYPE: DNA
<213> ORGANISM: Artificial Sequence
<220> FEATURE:
<223> OTHER INFORMATION: Synthetic - Sequence of HEX tail

<400> SEQUENCE: 11
gaaggtgacc aagttcatgc t                                           21

<210> SEQ ID NO 12
<211> LENGTH: 43
<212> TYPE: DNA
<213> ORGANISM: Artificial Sequence
<220> FEATURE:
<223> OTHER INFORMATION: Synthetic - Exemplary primer for detection of
      A. palmeri allele at Marker 1 comprising HEX tail

<400> SEQUENCE: 12
gaaggtgacc aagttcatgc tcgggcgtgg atggcctaaa aag                   43

<210> SEQ ID NO 13
<211> LENGTH: 43
<212> TYPE: DNA
<213> ORGANISM: Artificial Sequence
<220> FEATURE:
<223> OTHER INFORMATION: Synthetic - Exemplary primer for detection of
      non-A. palmeri allele at Marker 1 comprising FAM tail

<400> SEQUENCE: 13
gaaggtcgga gtcaacggat tcgggcgtgg atggcctaaa aca                   43

```
<210> SEQ ID NO 14
<211> LENGTH: 44
<212> TYPE: DNA
<213> ORGANISM: Artificial Sequence
<220> FEATURE:
<223> OTHER INFORMATION: Synthetic - Exemplary primer for detection of
      A. palmeri allele at Marker 2 comprising HEX tail

<400> SEQUENCE: 14
gaaggtgacc aagttcatgc taggaatgaa aaagtgttta gagt                44

<210> SEQ ID NO 15
<211> LENGTH: 44
<212> TYPE: DNA
<213> ORGANISM: Artificial Sequence
<220> FEATURE:
<223> OTHER INFORMATION: Synthetic - Exemplary primer for detection of
      non-A. palmeri allele at Marker 2 comprising FAM tail

<400> SEQUENCE: 15
gaaggtcgga gtcaacggat taggaatgaa aaagtgttta gagg                44

<210> SEQ ID NO 16
<211> LENGTH: 22
<212> TYPE: DNA
<213> ORGANISM: Artificial Sequence
<220> FEATURE:
<223> OTHER INFORMATION: Synthetic - Exemplary reverse primer for
      detection of Marker 2

<400> SEQUENCE: 16
ccctaaacaa aatctgccta ca                                        22

<210> SEQ ID NO 17
<211> LENGTH: 42
<212> TYPE: DNA
<213> ORGANISM: Artificial Sequence
<220> FEATURE:
<223> OTHER INFORMATION: Synthetic - Exemplary primer for detection of
      A. palmeri allele at Marker 3 comprising HEX tail

<400> SEQUENCE: 17
gaaggtgacc aagttcatgc taaattaacg ttaggaaagc gt                  42

<210> SEQ ID NO 18
<211> LENGTH: 42
<212> TYPE: DNA
<213> ORGANISM: Artificial Sequence
<220> FEATURE:
<223> OTHER INFORMATION: Synthetic - Exemplary primer for detection of
      non-A. palmeri allele at Marker 3 comprising FAM tail

<400> SEQUENCE: 18
gaaggtcgga gtcaacggat taaattaacg ttaggaaagc gg                  42

<210> SEQ ID NO 19
<211> LENGTH: 20
<212> TYPE: DNA
<213> ORGANISM: Artificial Sequence
<220> FEATURE:
<223> OTHER INFORMATION: Synthetic - Exemplary reverse primer for
      detection of Marker 3

<400> SEQUENCE: 19
actccgactt gatgagcttt                                           20
```

ASSAY FOR DETECTING PALMER AMARANTH DNA IN INDIVIDUAL AND MIXED SAMPLES

CROSS-REFERENCE TO RELATED APPLICATIONS

This application claims priority to U.S. Provisional Application No. 63/000,946 filed on Mar. 27, 2020, the contents of which is incorporated by reference in its entirety.

SEQUENCE LISTING

A Sequence Listing accompanies this application and is submitted as an ASCII text file of the sequence listing named "920171_00411_ST25.txt" which is 5 KB in size and was created on Mar. 24, 2021. The sequence listing is electronically submitted via EFS-Web with the application and is incorporated herein by reference in its entirety.

INTRODUCTION

*Amaranthus palmeri* (referred to by the common names Palmer amaranth, Palmer pigweed, and careless weed) is an invasive annual weed with a severe impact on agricultural systems. *A. palmeri* is native to the southwestern United States and northern Mexico but has spread across much of the United States, with the largest expansion into the Southeast and Midwest regions. *A. palmeri* has been added to the list of prohibited noxious weeds in multiple states due to its severe economic impact, particularly on the yield of row cropping systems. Effects on corn and soybean yields are most severe, with reports finding yield losses as high as 91% in corn (Massinga et al., 2001) and 68% in soybean (Klingaman and Oliver, 1994). Cotton, another cash crop impacted by *A. palmeri*, can also have its yield decreased by up to 54% in heavily infested fields (Morgan et al., 2001).

To prevent these losses, *A. palmeri* is generally controlled by heavy use of herbicides, such as ALS inhibitors and glyphosate. Unfortunately, in the last two decades, herbicide resistance has rapidly arisen in independent populations of *A. palmeri* across several herbicide modes-of-action. *A. palmeri* has been found with resistance to 5 different classes of herbicide, including glyphosate (Culpepper et al., 2006; Gaines et al., 2010), ALS inhibitors (KUpper et al., 2017; Nakka et al., 2017b), PPO inhibitors (Salas-Perez et al., 2017; Salas et al., 2016; Schwartz-Lazaro et al., 2017; Varanasi et al., 2018), HPPD-inhibitors (Chahal et al., 2018; Oliveira et al., 2018), and atrazine (Heap, 2019; Nakka et al., 2017a; Peterson et al., 2017). Additionally, populations with multiple resistance traits have been identified in numerous studies (Heap, 2019; Jhala et al., 2014; Kohrt et al., 2017; Küpper et al., 2017; Schwartz-Lazaro et al., 2017). The spread of these herbicide resistant traits is of great concern due to the rapid maturity, high pollen load, and prolific seed production of *A. palmeri*. The glyphosate resistance trait, in particular, has been shown to be transferred to susceptible populations under field conditions (Sosnoskie et al., 2012).

For these reasons, prevention of *A. palmeri* establishment is a high priority. The *Amaranthus* genus contains 75 species but, with the exception of *A. palmeri* and *A. tuberculatus*, most other Amaranths are of limited economic concern. Effective control efforts hinge on accurate and rapid identification of weed species. Unfortunately, morphological identification of *A. palmeri* in the field is a challenge, as several other Amaranths can easily be confused with Palmer (FIG. 1). Morphological identification is also not suited for identifying seeds, which were the source of several recent introductions in Minnesota and North Dakota. In response, commercially available genetic testing has become the standard for identifying *A. palmeri* in samples. However, these tests are limited due the lack of extensive genomic resources available for *Amaranthus* species.

One of the major pathways of introduction for Palmer Amaranth is through contaminated seed lots. This has led to the listing of *A. palmeri* on prohibited noxious seed lists of several states, such as Iowa, Ohio, Minnesota and South Dakota. Due to the difficulties in identifying *Amaranthus* seed morphologically, there has been a rapid adoption of genetic testing to identify *A. palmeri* contamination in pools of seed. Genetic testing is specifically required by some states before a sample can be certified as free from *A. palmeri* (Minnesota Department of Agriculture, 2020). This has created a large demand for high-throughput bulk testing methods that can be used to identify *A. palmeri* seed in seed mixes. However, the sensitivity of a genetic test determines the maximum number of seeds that can be processed as a single sample, and the currently available assays are limited in this regard. Thus, there remains a need in the art for methods of genotyping Amaranth that have improved sensitivity and can detect rare alleles in mixed genetic pools.

SUMMARY

Methods and kits for detecting the presence of *Amaranthus palmeri* plant material or determining if a sample contains *Amaranthus palmeri* plant material are provided herein. Methods for determining whether a sample contains *Amaranthus palmeri* plant material include providing a primer set which may include a first primer comprising SEQ ID NO: 1 or SEQ ID NO: 4, respectively that recognizes a first locus in the genome of *Amaranthus* and is specific to the sequence variant found in *Amaranthus palmeri*; a second primer comprising SEQ ID NO: 2 or SEQ ID NO: 5, respectively that recognizes the first locus in the genome of *Amaranthus* and is specific to the sequence variant found in all *Amaranthus* species other than *Amaranthus palmeri*, and a third primer that recognizes a second locus in the genome of *Amaranthus* and is specific to a sequence found in all *Amaranthus* species and is capable of acting as a reverse primer in a PCR reaction with either the primers of both SEQ ID NO: 1 and 2 or with the primers of both SEQ ID NO: 4 and 5. These primer sets are then combined with a sample comprising DNA derived from at least one *Amaranthus* plant to form a reaction mixture by contacting the primer set with the sample under conditions in which the first primer and second primer each form a primer pair with the third primer, such that the primer pairs bind to and amplify nucleotide sequences in the sample that are recognized by the primer pairs; the DNA in the sample is then amplified in the reaction mixture such that any DNA amplified using the first primer forms a first amplification product and any DNA amplified using the second primer forms a second amplification product; and finally determining if the first amplification product is present following amplification, wherein the presence of the first amplification product indicates that the sample contains *Amaranthus palmeri* plant material.

In another aspect, kits for determining relative abundance of *Amaranthus palmeri* DNA in a sample are provided. The kits include a first primer that recognizes a first locus in the genome of *Amaranthus* and is specific to the sequence variant found in *Amaranthus palmeri*, a second primer that recognizes the first locus and is specific to the sequence variant found in all *Amaranthus* species other than *Amaranthus palmeri*, and a third primer that recognizes a second locus in the genome of *Amaranthus* and is specific to a sequence found in all *Amaranthus* species. In these kits the first primer comprises SEQ ID NO: 1 and the second primer comprises SEQ ID NO: 2 or the first primer comprises SEQ ID NO: 4 and the second primer comprises SEQ ID NO: 5.

DETAILED DESCRIPTION

Figure 1:
FIG. 1 illustrates the fact that many *Amaranthus* species are morphologically similar, making species identification challenging. From left to right: *A. palmeri, A. powelii,* and *A. spinosus*.

The present invention provides methods and kits for screening for *Amaranthus palmeri* plant material. *A. palmeri* (also referred to as "Palmer amaranth" or simply "Palmer") is an important weed species that can contaminate seeds for sale (e.g., wildflowers, native grasses). *A. palmeri* has been listed as a prohibited noxious weed species in some US states, meaning that a seed lot containing *A. palmeri* may not be sold legally. *A. palmeri* seeds cannot be distinguished visually from those of other, non-noxious *Amaranthus* species, such as redroot pigweed (*Amaranthus retroflexus*), smooth pigweed (*Amaranthus hybridus*), and spiny amaranth (*Amaranthus spinosus*). Thus, genetic testing is commonly used to identify *A. palmeri* contamination.

The methods of the present invention were designed to work with diverse populations of Amaranth that have accumulated genetic distance through geographic isolation. Rather than utilize the *A. palmeri* genome sequences available in the NCBI database, which are limited in terms of geographic representation, the inventors utilized a genotyping by sequencing (GB S) approach to identify a large number of single nucleotide polymorphisms (SNPs) that exist within a panel of diverse *Amaranthus* populations. As used herein, the term "SNP" refers to a specific position in the genome at which several sequence variants exist within a population. The inventors were then able to identify SNPs that share a single "state" in all *A. palmeri* samples (i.e., they all have an "A", "G", "C", or "T" nucleotide at that specific genomic position) yet have a different state in all *Amaranthus* species other than *A. palmeri*. In the methods disclosed herein, these "*A. palmeri*-distinguishing SNPs" are used as genetic markers for screening for *A. palmeri* plant material. Specifically, these SNPs were used to design sets of primers that (i) specifically recognize DNA from *A. palmeri*, and (ii) specifically recognize DNA from all *Amaranthus* species other than *A. palmeri*. The methods of the present invention utilize these primers in polymerase chain reaction (PCR)-based assays (i) to determine whether a sample contains *A. palmeri* plant material or (ii) to genotype an *Amaranthus* plant. Compared to currently available assays, the methods disclosed herein are more sensitive, more robustly validated, easier to use, and less expensive per test.

Methods:

The present invention provides methods for determining whether a sample contains *Amaranthus palmeri* plant material. The methods comprise five steps (steps a-e). Step a comprises providing a primer set. The primer set comprises three primers: (i) a first primer that recognizes a first locus in the genome of *Amaranthus* and is specific to the sequence variant found in *Amaranthus palmeri*, (ii) a second primer that recognizes the first locus in the genome of *Amaranthus* and is specific to the sequence variant found in all *Amaranthus* species other than *Amaranthus palmeri*, and (iii) a third primer that recognizes a second locus in the genome of *Amaranthus* and is specific to a sequence found in all *Amaranthus* species. Within the primer set, the first primer comprises SEQ ID NO: 1 and the second primer comprises SEQ ID NO: 2 or the first primer comprises SEQ ID NO: 4 and the second primer comprises SEQ ID NO: 5. Step b comprises obtaining a sample comprising DNA derived from at least one *Amaranthus* plant. Step c comprises forming a reaction mixture by contacting the primer set with the sample under conditions in which the first primer and second primer each form a primer pair with the third primer, such that the primer pairs bind to and amplify nucleotide sequences in the sample that are recognized by the primer pairs. Step d comprises amplifying DNA in the sample, wherein any DNA amplified using the first primer forms a first amplification product and any DNA amplified using the second primer forms a second amplification product. Step e comprises detecting whether the first amplification product is present following amplification, wherein the presence of the first amplification product indicates that the sample contains *Amaranthus palmeri* plant material.

As is described above, the inventors used sequencing data from a diverse panel of *Amaranthus* plants to identify SNPs by which *Amaranthus palmeri* DNA can be distinguished from the DNA of all *Amaranthus* species other than *Amaranthus palmeri*. The inventors then designed primer sets that can be used to genotype these SNPs using a PCR-based assay. PCR is an in vitro method used to selectively amplify a specific DNA target sequence in a sample. PCR employs two main reagents: primers (i.e., short, single-stranded nucleic acid fragments that are complementary to the 5' and 3' ends of the target DNA sequence) and a DNA polymerase. In PCR, a repeated series of reaction steps, involving template denaturation, primer annealing, and the extension of the annealed primers by DNA polymerase, results in exponential amplification of the target sequence, which has termini that are defined by the 5' ends of the primers. (See Saiki et al., 1985, Science 230:1350 for a detailed description of PCR.)

PCR is commonly performed using a "reaction mixture" that comprises template DNA (typically 1-1000 ng), and at least about 25 pmol of each primer. The reaction mixture must also include deoxynucleoside triphosphates (dNTPs) and a nucleic acid polymerase. For example, a typical reaction mixture might include: 2 μl of DNA, 25 pmol of each primer, 2.5 μl of a suitable buffer, 0.4 μl of 1.25 μM dNTP, 2.5 units of Taq polymerase, and deionized water to a total volume of 25 µl. Notably, for the methods of the present invention, the template DNA is *Amaranthus* genomic DNA and the primers include the *A. palmeri*-distinguishing primers disclosed herein.

PCR utilizes a "nucleic acid polymerase", an enzyme that catalyzes the polymerization of nucleoside triphosphates. Generally, the enzyme will initiate synthesis at the 3'-end of the primer annealed to the target sequence, and will proceed in the 5'-direction along the template. Known DNA polymerases for use in PCR methods include, for example, *E. coli* DNA polymerase I, T7 DNA polymerase, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcus furiosus* (Pfu) DNA polymerase. The term "nucleic acid polymerase" also encompasses RNA polymerases. If the nucleic acid template is RNA, then "nucleic acid polymerase" refers to an RNA-dependent polymerization activity, such as a reverse transcriptase. Advantageously, the polymerase is a thermostable polymerase that is robust enough tolerate high-temperature PCR cycles (e.g., 95° C.) without compromising its enzymatic activity.

PCR is performed using a programmable thermal cycler. The length and temperature of each step of a PCR cycle, as well as the number of cycles, are adjusted according to the stringency requirements of the particular reaction. Annealing temperature and timing are determined both by the efficiency with which a primer is expected to anneal to a template and by the degree of mismatch (i.e., between the primer and template) that is to be tolerated. The ability to optimize the stringency of primer annealing conditions is well within the knowledge of one of moderate skill in the art. An annealing temperature of between 30° C. and 72° C. is typically used. An initial denaturation of the template molecules is normally performed for a period of time, such as 4 minutes, at between 92° C. and 99° C., followed by 20-40 cycles consisting of a denaturation step (94-99° C. for 15 seconds to 1 minute), annealing step (temperature determined as discussed above; 30 seconds-2 minutes), and extension step (72° C. for 1 minute). The final extension step is generally carried out for 4 minutes at 72° C., and may be followed by an indefinite (0-24 hour) hold at 4° C.

Once the PCR program is finished, a detection step is performed to determine whether the first amplification product is present in the sample. Detection may be performed using any method known in the art. Suitable methods of detection include, without limitation, sequencing (e.g., Sanger sequencing, single-molecule sequencing, second-generation high throughput sequencing, pyrosequencing), restriction fragment length polymorphism (RFLP) analysis, and quantitative PCR (qPCR). In some embodiments, detection is accomplished using kompetitive allele specific PCR (KASP; discussed further below).

The methods and kits of the present invention are designed to "genotype" the *A. palmeri*-distinguishing SNPs disclosed herein. As used herein, the term "SNP genotyping" refers to a process by which the identity of the nucleotide present at a SNP is assayed. The "primer sets" of the present invention comprise three primers, including two variant-specific primers that each recognize a single genomic locus (i.e., position) comprising a SNP. One variant-specific primer (i.e., the "first primer") is designed to specifically recognize the SNP variant present in *A. palmeri*, while the other variant-specific primer (i.e., the "second primer") is designed to specifically recognize DNA from all *Amaranthus* species other than *A. palmeri*. This is accomplished by designing the primers such that they hybridize to a genomic sequence that includes the SNP at its 3' end. The primer sets further comprise a common reverse primer (i.e., the "third primer") that recognizes a second locus, which has the same sequence in the genome of all *Amaranthus* species. Importantly, the reverse primer can form a primer pair with either or both of the variant-specific primers. As used herein, the term "primer pair" refers to two primers that anneal to the opposite ends of a target sequence on opposite strands, such that they form an amplification product when that target sequence is present in a reaction mixture that is subjected to PCR. Primers are typically 18 to 24 base pairs in length. However, primers of any length may be used with the present invention as long as they are capable of producing an amplification product via PCR. It is common practice for those of skill in the art to alter a primer set and/or PCR reaction conditions to optimize amplification.

Thus, the primer sets of the present invention comprise three primers that enable amplification of a target sequence that is either indicative of the presence of DNA from *A. palmeri* (i.e., if amplification occurs using the first primer, forming the first amplification product) or is indicative of the presence of DNA from any other *Amaranthus* species (i.e., if amplification occurs using the second primer, forming the second amplification product). In some embodiments, SNP genotyping involves simply determining whether the SNP variant associated with *A. palmeri* is present in the sample. In other embodiments, SNP genotyping further comprises determining whether the SNP variant associated with all *Amaranthus* species other than *A. palmeri* is present in the sample.

The methods of the present invention are performed on samples comprising DNA derived from at least one *Amaranthus* plant. As used herein, the term "*Amaranthus* plant" refers to any plant belonging to the genus *Amaranthus*. The sample may be obtained in any convenient matter from any tissue, callus, organ, seed, or part of a plant that is suspected to be an *Amaranthus* plant. In some embodiments, the sample includes DNA that is extracted from a collection of seeds. In other embodiments, the sample includes DNA that is extracted from the leaf of a single plant. Any DNA extraction method may be used to prepare the samples used with the present invention, as such methods are considered routine in the art. However, some plant tissues may require disruption (e.g., grinding) to allow for efficient extraction. For example, the inventors recommend the use of disruption methods such as grinding beads, liquid nitrogen, or an extended incubation in lysis buffer, and they advise that samples of disrupted *Amaranthus* seeds are visually inspected to ensure complete disruption.

The terms "plant," "plant material," or "plant part" are used broadly herein to refer to a plant at any stage of development or to part of a plant, including a plant cutting, a plant cell, a plant cell culture, a plant organ, a plant tissue, a plant seed, or a plantlet. A plant cell is the structural and physiological unit of the plant, comprising a protoplast and a cell wall. A plant cell can be in the form of an isolated single cell or aggregate of cells (e.g., a friable callus or a cultured cell) or can be part of a higher organized unit. Particularly useful parts of a plant include harvestable parts and parts that can be used for propagation of progeny plants. A harvestable part of a plant can be any useful part of a plant, for example, flowers, pollen, seedlings, tubers, leaves, stems, fruit, seeds, roots, and the like. A part of a plant useful for propagation includes, for example, seeds, fruits, cuttings, seedlings, tubers, rootstocks, and the like. The tissue culture will preferably be capable of regenerating plants.

In some embodiments, the methods further comprise quantifying the first amplification product and the second amplification product to calculate the abundance of *Amaranthus palmeri* DNA relative to total *Amaranthus* DNA in the sample. Quantification may be accomplished using a nucleic acid detection agent (e.g., a dye or probe). For example, quantification is commonly performed using quantitative PCR (qPCR; also known as real-time PCR), in which the production of an amplification product is monitored during the reaction (i.e., in real time), as opposed to at its end, as in conventional PCR. In qPCR, detection may be accomplished, for example, using (i) non-specific fluorescent dyes that intercalate into any double-stranded DNA (e.g., SYBR Green or LC-Green) or (ii) sequence-specific DNA probes that are labelled with a fluorescent reporter, which permit detection only after hybridization of the probe with its complementary sequence. Methods of quantifying PCR amplification products are considered routine in the art, and any known quantification methods may be used with the present invention.

One of the primary applications of the present invention is to identify *A. palmeri* contamination in pools of plant material using high-throughput bulk testing. Thus, in some embodiments, the sample comprises DNA from a plurality of *Amaranthus* plants. In particular embodiments, the sample comprises DNA from more than five, more than ten, more than 20, more than 50, more than 75, more than 100, more than 150 or even more than 200 *Amaranthus* plants.

Importantly, the methods disclosed herein can be used by the seed certification industry to reliably determine whether bulked *Amaranthus* seed samples contain *A. palmeri*. Several very common *Amaranthus* species are not noxious weeds (e.g., redroot pigweed, smooth pigweed, etc.), and seeds of the various *Amaranthus* species cannot be visually identified reliably. Thus, genetic testing is now commonly used to identify *A. palmeri* contamination in pools of seed. Advantageously, the methods described herein are sensitive enough to detect a single *A. palmeri* seed in a pool of 200 *Amaranthus* sp. seeds. This represents a substantial advance over similar methods that utilize a different genetic marker (i.e., the ITS marker), which can detect a single *A. palmeri* seed in a pool of up to five total seeds (see U.S. Pat. No. 9,963,750). These methods are thus not useful to detect small levels of *A. palmeri* contamination in a seed sample.

Additionally, the methods disclosed herein may also be used to genotype an *Amaranthus* plant. For this application, the sample comprises DNA from a single *Amaranthus* plant, and the method includes the additional step of detecting whether the second amplification product is present following amplification. In this case, (i) the presence of only the first amplification product indicates that the plant is *Amaranthus palmeri*; (ii) the presence of only the second amplification product indicates that the plant is an *Amaranthus* species other than *Amaranthus palmeri*; and (iii) the presence of both the first amplification product and the second amplification product indicates the plant is a hybrid of *Amaranthus palmeri* and another *Amaranthus* species.

This method of genotyping may be useful for determining the best method of control for a particular plant population. For example, one may use this method to genotype a large number of plants in a population. If the population is determined to comprise a high proportion of *Amaranthus palmeri* plants and/or hybrids thereof, more aggressive measures can be taken to reduce the growth of these unwanted plants. Exemplary eradication methods that may be utilized include, without limitation, physical removal, application of biological controls (e.g., insects, fungi, microbes, etc.), application of naturally occurring compositions that affect plant growth, and chemical applications (e.g., herbicides). For example, using this information, weed managers can make more informed decisions regarding herbicide type and application rates (e.g., choosing specific herbicides and rates to control hybrid individuals only when they are confirmed to be present).

The methods of the present invention can be performed using any known PCR-based method. Suitable PCR-based methods include, without limitation, standard PCR, quantitative PCR (qPCR), PCR-restriction fragment length polymorphism (PCR-RFLP), asymmetrical PCR, strand displacement amplification (SDA), rolling circle amplification (RCA), transcript mediated amplification (TMA), self-sustained sequence replication (3 SR), and ligase chain reaction (LCA). However, in preferred embodiments, the methods involve the use of a reporter system for easy detection of the amplified product(s). For instance, in one such reporter system: (i) the first primer further comprises a first reporter sequence and the second primer further comprises a second reporter sequence; (ii) the reaction mixture of step (c) further comprises a first reporter molecule that binds to the first reporter sequence in the first amplification product and a second reporter molecule that binds to the second reporter sequence in the second amplification product; and (iii) binding of the first reporter molecule produces a first detectable signal and binding of the second reporter molecule produces a second detectable signal in step (d).

As used herein, the term "reporter sequence" is used to refer to a nucleotide sequence that is specifically bound by a "reporter molecule". A "reporter molecule" is a molecule that is capable of creating a detectable signal upon binding to the reporter sequence. Suitable reporter molecules include, for example, dyes and probes. Suitable "detectable signals" created by the binding of the reporter molecule to the reporter sequence include, without limitation, fluorescent signals, luminescent signal, colorimetric signal, wavelength absorbance, or radioactive signals.

In a particular preferred embodiment, the reporter system used with the present invention is based on kompetitive allele specific PCR (KASP), a fluorescence-based version of PCR that is commonly used for genotyping SNPs. KASP is able to discriminate between two variants of a SNP using two forward primers, one specific to each variant (i.e., the first primer and the second primer), and a common reverse primer that forms a primer pair with both forward primers (i.e., the third primer). In addition to a sequence that hybridizes with the target SNP, each forward primer also comprises a sequence (referred to as a "reporter sequence" or "tail sequence") that hybridizes with a different fluorescent reporter. In KASP, the PCR reaction mixture includes two fluorescence resonance energy transfer (FRET) cassettes that comprise a fluorescent reporter molecule linked to an oligonucleotide, which is complementary to, and capable of hybridizing with, one of the reporter sequences. A fluorescent reporter molecule is freed from a quencher molecule if the connected oligonucleotide of the reported molecule hybridizes to the reporter sequence. Thus, if the sequence recognized by a forward primer is present in the sample, it is amplified and the corresponding fluorescent reporter molecule creates a detectable signal. This signal is detected at the end of the assay using a qPCR machine. See, e.g., Yan et al. "Introduction of high throughput and cost effective SNP genotyping platforms in soybean" Plant Genetics, Genomic and Biotechnology 2(1): 90-94 (2014); Semagn et al. "Single nucleotide polymorphism genotyping using Kompetitive Allele Specific PCR (KASP): overview of the technology and its application in crop improvement" Molecular Breeding 33(1): 1-14 (2013). Thus, detection of one fluorescent signal or the other indicates the presence of material from a plant of one of the two species groups (i.e., *Amaranthus palmeri* or an *Amaranthus* species other than *Amaranthus palmeri*), whereas the presence of both signals indicates the presence of material from plants of both species group or from a hybrid plant.

With KASP, the most commonly used fluorescent reporters are 6-carboxyfluorescein (FAM) and 6-carboxy-2',4,4',5',7,7'-hexachlorofluorescein (HEX) fluorophores. Thus, in some embodiments, the first detectable signal is produced by a FAM fluorophore and the second detectable signal is produced by a HEX fluorophore. In this embodiment, detection of a FAM signal indicates that the sample contains *Amaranthus palmeri* plant material, while detection of a HEX signal indicates that the sample contains plant material from an *Amaranthus* species other than *Amaranthus palmeri*. However, any convenient means of producing a detectable signal may be used with the present invention. Other suitable fluorescent reporter molecules include, without limitation, tetrachlorofluorescein (TET), cyan florescent protein, yellow fluorescent protein, luciferase, SyBR Green I, ViC, CAL Fluor Gold 540, ROX Texas Red, CAL Fluor Red 610, CYS, Quasar 670, and Quasar 705.

The present inventors have designed primers for the detection of two genetic markers that distinguish *A. palmeri* plant material from non-*A. palmeri* plant material. These markers are referred to herein as Marker 2, and Marker 3. Marker 1 is a previously developed marker that may be used in combination with the two markers developed here. In some instances, it may be advantageous to detect multiple genetic markers in the sample. For instance, by combining the results obtained for multiple genetic markers, the species group assignment may be made with greater accuracy and confidence. In these instances, the process can employ additional primer sets that comprise different primers such that they target a different genetic marker (i.e., a SNP found at different loci). For example, in some embodiments, the method is performed using a first primer set on a first portion of the sample and a second primer set on a second portion of the sample. In other embodiments, the method is performed using a first primer set on a first portion of the sample, a second primer set on a second portion of the sample, and a third primer set on a third portion of the sample. However, the method may be performed using any number of additional primer sets on additional portions of the sample. Suitably, in methods in which two or more genetic markers are detected, at least two of the following primer sets are utilized: (a) a primer set in which the first primer comprises SEQ ID NO: 1 and the second primer comprises SEQ ID NO: 2, which are designed to detect the *A. palmeri* allele at Marker 2 and the non-*A. palmeri* allele at Marker 2, respectively; (b) a primer set in which the first primer comprises SEQ ID NO: 4 and the second primer comprises SEQ ID NO: 5, which are designed to detect the *A. palmeri* allele at Marker 3 and the non-*A. palmeri* allele at Marker 3, respectively; and (c) a primer set in which the first primer comprises SEQ ID NO: 7 and the second primer comprises SEQ ID NO: 8, which are designed to detect the *A. palmeri* allele at Marker 1 and the non-*A. palmeri* allele at Marker 1, respectively.

The third primer included in the primer set(s) used with the present invention may be any primer that forms a primer pair with both the first primer and the second primer. Suitably, to ensure that the primer pair sufficiently amplify the target sequence, the third primer should have a melting temperature ($T_m$) that is within 5° C. of the $T_m$ of both the first primer and the second primer. As used herein the term "melting temperature" or "$T_m$" refers to the temperature at which a polynucleotide dissociates from its complementary sequence. Generally, the $T_m$ is defined as the temperature at which one-half of the Watson-Crick base pairs in a double stranded nucleic acid molecule are broken or dissociated (i.e., are "melted") while the other half of the Watson-Crick base pairs remain intact in a double stranded conformation. In other words, the $T_m$ is the temperature at which 50% of the nucleotides of two complementary sequences are annealed (double strands) and 50% of the nucleotides are denatured (single strands). $T_m$ therefore defines a midpoint in the transition from double-stranded to single-stranded nucleic acid molecules (or, conversely, in the transition from single-stranded to double-stranded nucleic acid molecules). $T_m$ can be estimated by a number of methods, for example, by a nearest-neighbor calculation (Wetmur, J. G. 1991. DNA probes: applications of the principles of nucleic acid hybridization. Crit Rev Biochem Mol Biol 26: 227-259,) by commercially available programs (e.g., Oligo™ Primer Design), and by programs available freely on the internet. Alternatively, the $T_m$ can be determined through experimentation. For example, double-stranded DNA binding or intercalating dyes, such as Ethidium bromide or SYBR-green can be used in a melting curve assay to determine the $T_m$ of the nucleic acid empirically. Additional methods for determining the $T_m$ of a nucleic acid are well known in the art (see, e.g., U.S. Pat. No. 8,455,190). The $T_m$ of a primer is directly affected by the length and nucleotide composition of the primer: Longer strands have higher melting temperatures, as do sequences with higher G and C content. A $T_m$ of about 52° C. to about 58° C. is typically considered a good starting range for a primer, but may need to be adjusted depending on the particular reaction conditions. The annealing temperature used in a PCR reaction must be adjusted to suit the $T_m$ of the primers. The annealing temperature can also be changed during the course of the assay in a method called touchdown PCR, which is a well-known method in the art. Accordingly, it is considered good practice to design primer pairs such that $T_m$ difference of the primers is no greater than 5° C.

Additionally, to ensure that the entire amplification product (commonly referred to as the "amplicon") is produced within the time limit of the extension step, the third primer should recognize a second locus that is within 1000 bp of the first locus (i.e., the locus recognized by both the first primer and the second primer). Ideal amplicon length depends on many variables. For standard PCR, amplicons are generally designed to be between 200-1000 bp. For quantitative PCR (qPCR), amplicons typically range from 75-150 bp. It is unlikely that an amplicon will be too short. However, amplicons that are longer than 1000 bp may need extra time to be completed within the extension step. The time required to produce an amplicon depends on the polymerization rate of the polymerase used in the reaction, but, generally, about 1 minute of extension time is required per kb of amplicon.

In the Examples, the inventors used a panel of diverse *Amaranthus* populations to identify novel genetic markers (i.e., SNPs) that can be used to screen for *A. palmeri* plant material in a sample. They refer to these novels SNPs as "Marker 2" and "Marker 3". The inventors assay Marker 2 using a primer set in which the first primer comprises SEQ ID NO: 1, the second primer comprises SEQ ID NO: 2, and the third primer comprises SEQ ID NO: 3, whereas they assay Marker 3 using a primer set in which the first primer comprises SEQ ID NO: 4, the second primer comprises SEQ ID NO: 5, and the third primer comprises SEQ ID NO: 6. Thus, either one or a combination of both of these primer sets may be used with the present invention.

The inventors compare these novel markers to a previously disclosed genetic marker, referred to as "ITS" or "Marker 1" (see U.S. Pat. No. 9,963,750, which is incorporated by reference in its entirety). The ITS marker, which comprises SNPs found within the Internal Transcribed Spacer (ITS) region of the *Amaranthus* genome, enables the identification of each of nine *Amaranthus* species. Specifically, a double SNP in this locus comprising two consecutive nucleotides differentiates *A. palmeri* from the other eight species. In the Examples, the ITS marker is assayed using a primer set in which the first primer comprises SEQ ID NO: 7, the second primer comprises SEQ ID NO: 8, and the third primer comprises SEQ ID NO: 9. The ITS marker can be used with the present invention in combination with Marker 2, in combination with Marker 3, or in combination with both Marker 2 and Marker 3.

Kits:

The present invention also provides kits for determining the relative abundance of *Amaranthus palmeri* DNA in a sample. The kits comprise a primer set comprising: (a) a first primer that recognizes a first locus in the genome of *Amaranthus* and is specific to the sequence variant found in *Amaranthus palmeri*, (b) a second primer that recognizes the first locus and is specific to the sequence variant found in all *Amaranthus* species other than *Amaranthus palmeri*, and (c) a third primer that recognizes a second locus in the genome of *Amaranthus* and is specific to a sequence found in all *Amaranthus* species. Within the primer set, the first primer comprises SEQ ID NO: 1 and the second primer comprises SEQ ID NO: 2 or the first primer comprises SEQ ID NO: 4 and the second primer comprises SEQ ID NO: 5.

In some embodiments, the kits include a reporter system, such as those described above. Thus, in some embodiments, the first primer further comprises a first reporter sequence and the second primer further comprises a second reporter sequence. In some embodiments, the kit further comprising a first reporter molecule that binds to the first reporter sequence and a second reporter molecule that binds to the second reporter sequence, wherein binding of the first reporter molecule produces a first detectable signal and binding of the second reporter molecule produces a second detectable signal. In preferred embodiments, the first reporter molecule and second reporter molecule are supplied as FRET cassettes. In particularly preferred embodiments, the first detectable signal is produced by a FAM fluorophore and the second detectable signal is produced by a HEX fluorophore or vice versa.

To increase the reliability of the kits, the kits of the present invention may further comprise a positive control for *Amaranthus palmeri* DNA and/or a positive control for DNA from all *Amaranthus* species other than *Amaranthus palmeri*. A positive control should comprise a DNA sequence that is recognized by the corresponding primer, i.e., a positive control for *Amaranthus palmeri* should comprise a sequence recognized by the first primer and a positive control for all *Amaranthus* species other than *Amaranthus palmeri* should comprise a sequence recognized by the second primer. The positive control(s) may be provided as isolated DNA (e.g., commercially ordered polynucleotides) or within a plasmid (i.e., to facilitate amplification in *E. coli*).

The kits may further comprise additional reagents that may be used with the methods disclosed here. For example, the kits may comprise standard reagents used for PCR including, without limitation, deoxynucleotide triphosphates, DNA polymerase, $MgCl_2$, and/or buffers. The kits may also comprise an instruction manual and other information that may be useful for performing the methods disclosed herein.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

*A. palmeri* is an aggressive and prolific weed species that has major impact on agricultural yield. Morphologically distinguishing *A. palmeri* from other *Amaranthus* species is difficult, especially when it is not flowering, which has led to the use of genetic testing becoming the standard for *Amaranthus* species identification.

In the following Example, the present inventors describe an improved genetic test based on novel *A. palmeri*-distinguishing single nucleotide polymorphisms (SNPs). To develop this test, the inventors utilized GBS (Genotyping by Sequencing) approaches to generate many polymorphic nucleotide calls from a panel of diverse *Amaranthus* populations. These SNPs were screened to identify SNPs that share a single state in all *A. palmeri* samples (i.e. an 'A', 'G', 'C', or 'T' nucleotide) yet have a different state in all other evaluated *Amaranthus* spp. They then designed a KASP (kompetetive allele specific polymerase chain reaction) genotyping assay based on these loci and validated it across a diverse panel of *Amaranthus* spp. both for individual plants and mixed seed samples. Notably, this panel, which included 20 populations of *A. palmeri* along with eight other *Amaranthus* species, is the largest and most genetically diverse panel of *Amaranthus* samples to date.

The sensitivity of the three tests the inventors developed ranged from 99.8 to 100%, and the specificity ranged from 99.59 to 100%. Accuracy for all three tests was >99.7%. Furthermore, the inventors showed that all three tests are capable of reliably detecting a single *A. palmeri* seed in a pool of 200 *Amaranthus* sp. seeds. This represents a marked improvement over existing commercial assays in sensitivity, robust validation, ease of use, and cost per test.

Materials and Methods:
Sampling Design and DNA Extraction

To assess the performance of our markers, a wide variety of *Amaranthus* seed was obtained from collaborators and from the USDA germplasm repository (GRIN) that cover a wide geographic area (summarized in Table 1). Twenty populations of *A. palmeri* were obtained (Table 2), along with smaller coverage from eight other related species (Table 3). Representation of *A. blitoides* was limited due to poor seed germination, a documented trait of that species (Steckel et al., 2004).

TABLE 1

Sampling structure of *Amaranthus* populations. Nine species were sampled, with a focus on *A. palmeri* and *A. tuberculatus*.

| Species | # of Populations |
|---|---|
| A. palmeri | 24 |
| A. spinosis | 5 |
| A. albus | 5 |
| A. blitoides | 2 |
| A. arenicola | 5 |
| A. tuberculatus | 10 |
| A. hybridus | 5 |
| A. powelii | 5 |
| A. retroflexus | 5 |

TABLE 2

Sampling *A. palmeri* populations. Twenty populations were tested from across the United States, 2 from Africa, 1 from Brazil, and 1 from the native range in Mexico.

| Species | Population | Samples |
|---|---|---|
| A. palmeri | AR | 20 |
| A. palmeri | AZR | 20 |
| A. palmeri | AZS | 20 |
| A. palmeri | BRAZIL | 20 |
| A. palmeri | CA | 21 |
| A. palmeri | COS | 20 |
| A. palmeri | DE | 20 |
| A. palmeri | GAR | 20 |
| A. palmeri | GAS | 20 |
| A. palmeri | IL | 20 |
| A. palmeri | KS | 20 |
| A. palmeri | MALI | 18 |
| A. palmeri | MD | 20 |
| A. palmeri | MEX | 20 |
| A. palmeri | MN | 20 |
| A. palmeri | MS | 20 |
| A. palmeri | NES | 18 |
| A. palmeri | NM2012 | 20 |
| A. palmeri | NM2013 | 20 |
| A. palmeri | SEN | 19 |
| A. palmeri | TNR | 18 |
| A. palmeri | TX | 20 |
| A. palmeri | WI2011 | 20 |
| A. palmeri | WI2015 | 20 |

TABLE 3

Sampling of non-Palmer *Amaranthus* populations. Eight non-Palmer species were sampled with a focus on Waterhemp (*A. tuberculatus*).

| Species | Population | Samples |
|---|---|---|
| A. albus | ALBUS1 | 18 |
| A. albus | ALBUS2 | 18 |
| A. albus | ALBUS3 | 19 |
| A. albus | ALBUS4 | 12 |
| A. albus | ALBUS5 | 20 |
| A. arenicola | AREN3 | 19 |
| A. arenicola | AREN4 | 20 |
| A. arenicola | AREN5 | 19 |
| A. arenicola | AREN6 | 19 |
| A. arenicola | AREN7 | 20 |
| A. blitoides | BLIT1 | 20 |
| A. blitoides | BLIT5 | 17 |
| A. hybridus | HYB1 | 18 |
| A. hybridus | HYB7 | 8 |
| A. hybridus | HYB9 | 20 |
| A. hybridus | HYB10 | 19 |
| A. hybridus | HYB13 | 20 |
| A. powelii | POW1 | 19 |
| A. powelii | POW2 | 20 |
| A. powelii | POW6 | 19 |
| A. powelii | POW7 | 18 |
| A. powelii | POW9 | 17 |
| A. retroflexus | RETRO1 | 18 |
| A. retroflexus | RETRO2 | 20 |
| A. retroflexus | RETRO5 | 20 |
| A. retroflexus | RETRO9 | 20 |
| A. retroflexus | RETRO12 | 19 |
| A. spinosus | SPIN1 | 18 |
| A. spinosus | SPIN4 | 19 |
| A. spinosus | SPIN5 | 18 |
| A. spinosus | SPIN7 | 17 |
| A. spinosus | SPIN9 | 14 |
| A. tuberculatus | TUB1 | 19 |
| A. tuberculatus | TUB2 | 20 |
| A. tuberculatus | TUB8 | 20 |
| A. tuberculatus | TUB9 | 20 |
| A. tuberculatus | TUB11 | 17 |
| A. tuberculatus | TUB12 | 20 |
| A. tuberculatus | TUB13 | 19 |

TABLE 3-continued

Sampling of non-Palmer *Amaranthus* populations. Eight non-Palmer species were sampled with a focus on Waterhemp (*A. tuberculatus*).

| Species | Population | Samples |
|---|---|---|
| *A. tuberculatus* | TUB14 | 20 |
| *A. tuberculatus* | TUB15 | 20 |
| *A. tuberculatus* | TUB16 | 20 |

Seeds were grown in a greenhouse for 1-2 months, after which leaves were harvested and dried with silica for long-term storage. DNA was extracted from a total of 50 individuals per population, with 20 individuals to be used for sequencing and 20 more for validation testing. DNA extraction was performed using the Qiagen Biosprint DNA extraction kit. The standard protocol was followed with the addition of 1% polyvinylpyrrolidone (PVP) to the RTL buffer to assist in removing phenolics. Samples were normalized to 10 ng/uL for use in all KASP tests. After removal of samples for quality control, a total of 817 samples met the standards for GBS submission. Additional samples were extracted until we had 1250 samples for validation testing.

Design and Validation of KASP Markers

DNA samples from all populations were submitted to the University of Minnesota Genomics Center for Genotyping by Sequencing (GBS). Raw reads were preprocessed using bcl2fastq and Trimmomatic v0.33 (www.usadellab.org/cms/?page=trimmomatic) (Bolger et al., 2014). The cleaned reads were aligned to the *A. hypochondriacus* genome assembly using Burrows-Wheeler Aligner (BWA) v0.7.17-r1188 under standard parameters for unpaired Illumina reads (bio-bwa.sourceforge.net) (Li and Durbin, 2009). SNP calling was conducted using Freebayes v1.2.0 (github.com/ekg/freebayes) (Garrison and Marth, 2012) and filtering was conducted using VCFtools v0.1.16 (vcftools.sourceforge.net/) (Danecek et al., 2011) under the following parameters: removed all variants with minor allele frequency<1%, variants with genotype rates<95%, and samples with genotype rates<50%. The filtered VCF file had a total of 274,520 SNPs across 30,186 loci. SNP calls were sorted by species using the R package vcfR v1.9.0 (cran.r-project.org/package=vcfR) in order to identify SNPs that were unique to the *A. palmeri* genome. Of 274,520 SNPs 111,546 were conserved across all *A. palmeri* individuals. *A. palmeri* conserved SNPs were then filtered against non-*A. palmeri* populations to identify potential target sites where the *A. palmeri* state did not match any non-*A. palmeri* individuals. Out of 51 potential species diagnostic SNPs we selected nine candidate sites for marker development and preliminary validation testing based on marker specificity and guanine-cytosine content (GC %) in marker regions. Of these nine candidate loci, the three demonstrating the most consistent performance were used to design a suite of KASP markers and subjected to full validation testing.

One of the diagnostic loci (Marker 1) had been previously identified for species identification and is included herein to assess its performance against a more rigorous validation panel. The other two sets of primers (Markers 2 and 3, both located on Scaffold 10) are novel discoveries and are presented here for the first time. KASP markers were developed for each candidate locus using HEX and FAM fluorescent dyes according to the method set forth by Patterson et al. (*Front Plant Sci* 8:1-10 (2017)). Each marker set consists of two species-specific forward primers and one universal reverse primer. The forward primer specific to the *A. palmeri* SNP had the FAM dye tail and the non-*A. palmeri* primer had the HEX dye tail. One reverse primer was designed for each SNP assay within 100 bp downstream of the diagnostic SNP, with priority given to matching melting temperature ($T_m$) value and forward primer binding site proximity.

The primer mix for the three markers in the assay for each SNP consisted of species-specific primers (18 μL each), universal primer (45 μL), and water (69 μL). Primer mix (11.88 μL) was combined with low-ROX KASP master mix (432 μL) (LGC Genomics, www.lgcgroup.com). Primer mix/master mix combination (4 μL), was plated into each well along with sample DNA (4 μL at 5-20 ng μL−1). PCR was run for a total of 28 cycles, with a nine-step touchdown. Endpoint readings were taken at on a Roche Lightcycler 480 II 465-510 and 533-580 nm, corresponding to HEX and FAM dyes. Raw fluorescent signals were classified using centroid-based [unweighted pair group method centroid (UPGMC)] hierarchical clustering and plotted in R using the ggplot2 package. Minimum fluorescence intensity for assigning a call was set to 20% relative to the highest fluorescence reading on the plate. This process was repeated for each of the three markers tested. Primer sequences and PCR temperatures are reported below (Table 4).

TABLE 4

Primer sets for three species diagnostic KASP assays. *A. palmeri* primer sequences include a FAM tail and non-*A. palmeri* sequences include a HEX tail. Reverse primer is unlabeled.

| Marker#/Locus | *A. palmeri* primer | Non-*A. palmeri* primer | Reverse primer | Tm (° C.) | #cycles |
|---|---|---|---|---|---|
| Marker 1 ITS | GAAGGTGACC AAGTTCATGCT CGGGCGTGGAT GGCCTAAAAA G (SEQ ID NO: 12) | GAAGGTCGGAGT CAACGGATTCGG GCGTGGATGGCC TAAAACA (SEQ ID NO: 13) | ACCAATCGC CGCAGCAGC (SEQ ID NO: 9) | 65° C.-57° C. | 24 |
| Marker 2 SSCAFFOLD_10_5769538 | GAAGGTGACC AAGTTCATGCT AGGAATGAAA AAGTGTTTAGA GT (SEQ ID NO: 14) | GAAGGTCGGAGT CAACGGATTAGG AATGAAAAAGTG TTTAGAGG (SEQ ID NO: 15) | CCCTAAACA AAATCTGCCT ACA (SEQ ID NO: 16) | 61° C.-55° C. | 28 |

TABLE 4-continued

Primer sets for three species diagnostic KASP assays. *A. palmeri* primer sequences include a FAM tail and non-*A. palmeri* sequences include a HEX tail. Reverse primer is unlabeled.

| Marker#/Locus | *A. palmeri* primer | Non-*A. palmeri* primer | Reverse primer | Tm (° C.) | #cycles |
|---|---|---|---|---|---|
| Marker 3 SSCAFFOLD_10_6327665 | GAAGGTGACC AAGTTCATGCT AAATTAACGTT AGGAAAGCGT (SEQ ID NO: 17) | GAAGGTCGGAGT CAACGGATTAAA TTAACGTTAGGA AAGCGG (SEQ ID NO: 18) | ACTCCGACTT GATGAGCTTT (SEQ ID NO: 19) | 61° C.-55° C. | 28 |

Validation performance was scored by comparing hierarchical cluster assignment with the species identification provided by the seed supplier. Two populations were suspected to be mislabeled by the seed supplier based on morphology of the mature plant, AREN6 (*A. arenicola* provided by GRIN as PI 667167, LP 146) and WI2015 (*A. palmeri* collected in Wisconsin in 2015). These two populations were removed from the validation pool. All remaining calls were assigned to a binary classification, either correct or incorrect, which was used to construct a confusion matrix. Standard diagnostic performance parameters were calculated based on the confusion matrix.

Detection Threshold of the KASP Assays

Detection threshold testing was conducted using a mix of *A. palmeri* and *A. tuberculatus* seeds, with both species acquired from GRIN. *Amaranthus tuberculatus* was chosen as a closely related dioecious species that is widespread across the Midwest, not a prohibited noxious weed in Midwest states, and likely to also be present in commercial seed lot weed seed purity tests. *Amaranthus tuberculatus* is also used for comparison against *A. palmeri* in an existing genetic test (Murphy et al., 2017). DNA extraction from seed pools was conducted using the MPBio FastDNA plant kit. Extraction protocol was modified with an overnight incubation period to soften the seed coat before disruption. Total grinding time for 200 seed samples was 8 min (Qiagen Tissuelyser II), with visual inspection every 2 min until total sample disruption was observed. Threshold testing was conducted at 0.5% and 1% contamination level (Table 5) using a modified PCR primer mix (20 µL of *A. palmeri* primers and 3 µL of non-*A. palmeri* primers) to maximize separation between *A. tuberculatus* and low *A. palmeri* samples. PCR was run for 40 cycles to ensure maximum cluster separation. Coordinates of data points were subjected to arctan transformation before plotting in R using the ggplot2 package.

TABLE 5

Structure of bulk seed testing to determine detection level of our assays.

| *A. palmeri* seeds | *A. tuberculatus* seeds | Percent *A. palmeri* |
|---|---|---|
| 0 | 50 | 0 |
| 1 | 199 | 0.5 |
| 1 | 99 | 1 |
| 100 | 0 | 100 |

Independent Validation of the KASP Assays

The three KASP markers were independently tested in the molecular weed science laboratory at Colorado State University, Fort Collins, CO, USA, including independent seed DNA extractions and primer synthesis following the methods described earlier.

Figure 2:
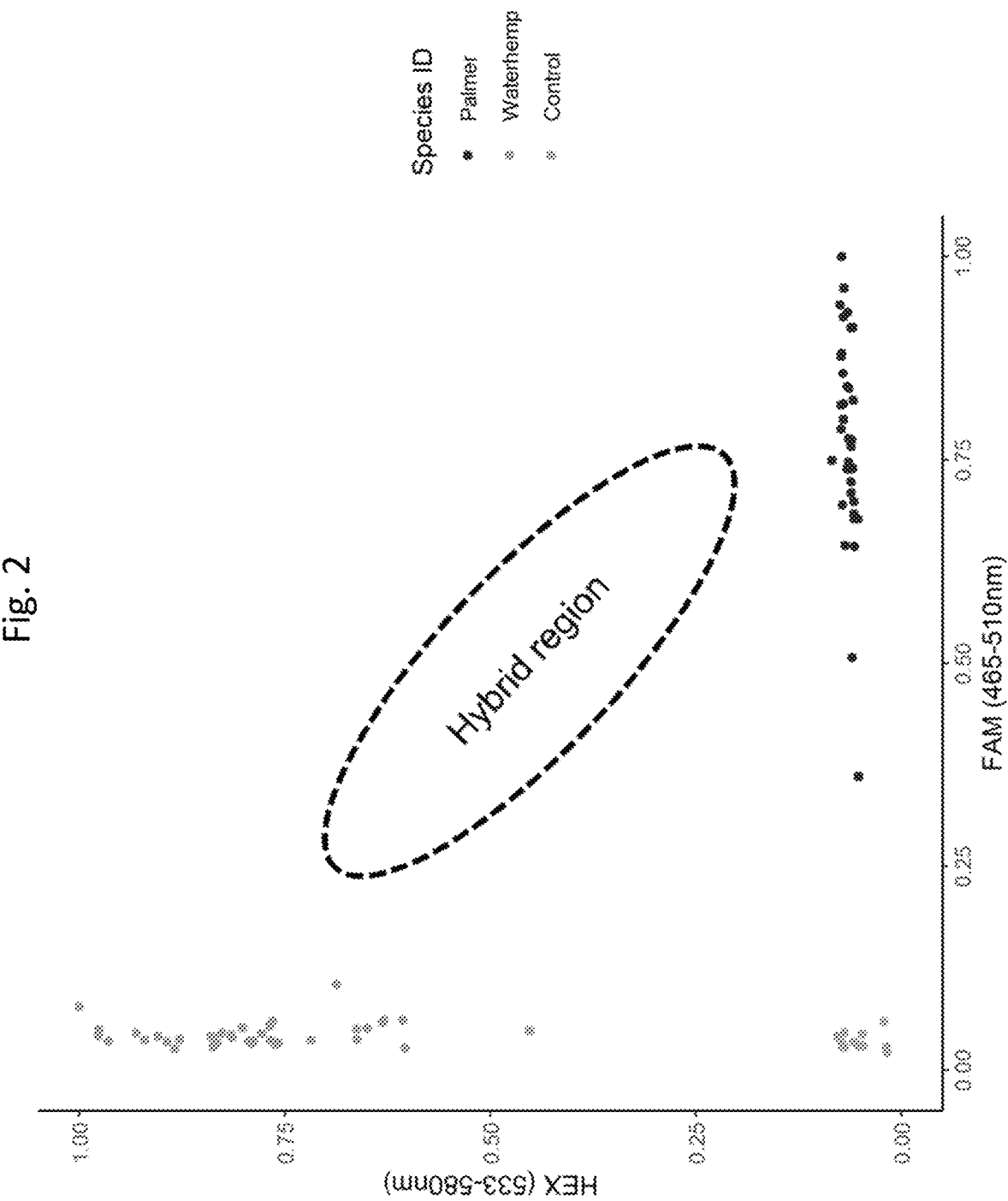
FIG. 2 shows an example of the output of a KASP marker on individual samples of *A. palmeri* (Palmer) and *A. tuberculatus* (Waterhemp). The controls contain no DNA from either species (i.e., non-template control (NTC)). The region for potential hybrid individuals is indicated by a dashed ellipse.

Results:

All three KASP markers were capable of reliably distinguishing between *A. palmeri* individuals and other *Amaranthus* spp. We validated marker #1 against a panel of 1248 total individuals, including 510 *A. palmeri* and 738 non-*A. palmeri*. FIG. 2 shows a representative result of a single plate with both *A. palmeri* and non-*A. palmeri* samples. Performance of the marker was high, with 100% of Palmer individuals being correctly identified. Overall accuracy was 99.76%, with a very low false-positive rate as three out of 738 non-*A. palmeri* individuals classified as *A. palmeri*. Markers 2 and 3 performed similarly, with 99.84% and 99.92% accuracy, respectively. The confusion matrix and associated statistics for each marker can be found below (Tables 6-8).

TABLE 6

Confusion matrix for Marker 1.

|  |  | True Condition | |
|---|---|---|---|
|  |  | Palmer | Not Palmer |
| Assay Call | Palmer | 510 | 3 |
|  | Not Palmer | 0 | 735 |

TABLE 7

Confusion matrix for classification of Marker 2.

|  |  | True Condition | |
|---|---|---|---|
|  |  | Palmer | Not Palmer |
| Assay Call | Palmer | 512 | 2 |
|  | Not Palmer | 0 | 742 |

TABLE 8

Confusion matrix for classification of Marker 3.

|  |  | True Condition | |
|---|---|---|---|
|  |  | Palmer | Not Palmer |
| Assay Call | Palmer | 511 | 0 |
|  | Not Palmer | 1 | 741 |

Figure 3:
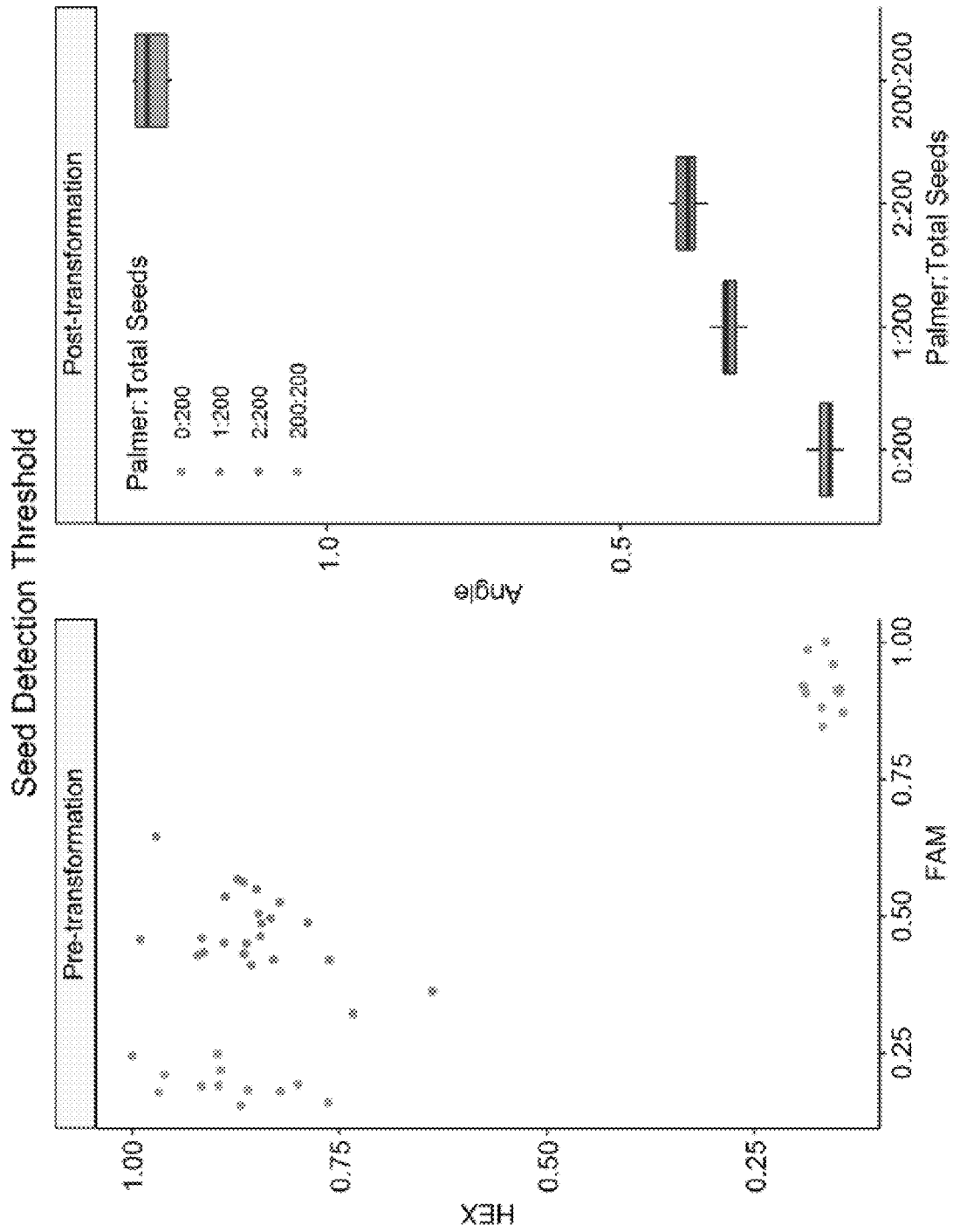
FIG. 3 shows the seed detection threshold pre- and post-transformation. Arctan transformation converts raw HEX-FAM fluorescence reads (left) into estimates of data point trajectory relative to the y-axis (right). Seed pool contaminated with *Amaranthus palmeri* have a significantly higher angle value than non-contaminated samples (*A. tuberculatus*).
Figure 4:
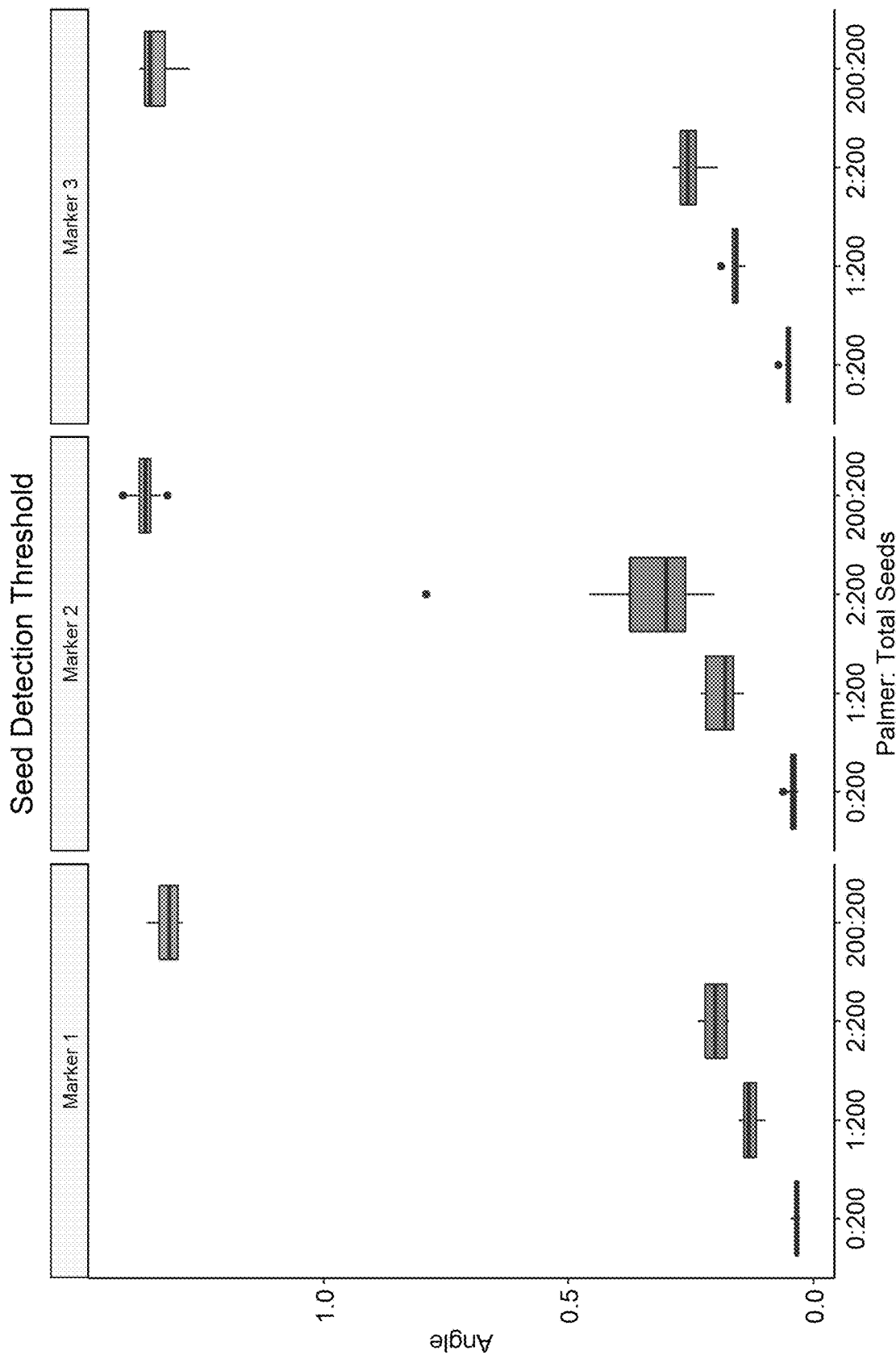
FIG. 4 shows the results of bulk testing of 200 seeds, which demonstrate reliable detection of *A. palmeri* (Palmer) against *A. tuberculatus*. All three markers are able to discriminate between 0:200 *A. palmeri* (100% *A. tuberculatus*) and 1:200 *A. palmeri* contamination levels (p<0.0001).

An assessment of assay sensitivity was conducted on all three markers by running mixed samples of *Amaranthus* spp. seeds. The diagnostic criteria for all three markers are shown in Table 9. Pure samples of *A. palmeri* and *A. tuberculatus* were run alongside samples with 2:200 and 1:200 *A. palmeri* seed. Reliable tissue disruption protocols were developed for 100 and 200 seed samples on the Qiagen TissueLyser II, consisting of up to 8 min of total disruption time. A modified KASP reaction mixture with reduced non-*A. palmeri* primers yielded consistent results; arctan transformed data allows us to identify significant separation between *A. tuberculatus* only pools and samples with one *A. palmeri* seed and 199 *A. tuberculatus* seeds (FIG. 3). This performance was consistent across all three markers (P<0.001 in all cases) (FIG. 4). These protocols were replicated by a second laboratory at Colorado State University that tested the same primer designs on the Bio-Rad C1000 Touch Thermal Cycler with CFX96 Real-Time PCR Detection System. To ensure independent replication, the personnel performing these trials were not involved in the development of the protocols. Results from the Colorado State University team were consistent with the results from University of Minnesota: all three markers provided significant discrimination between *A. tuberculatus* and 1:200 *A. palmeri* samples (P<0.0001 in all cases). We have demonstrated that all three marker sets developed can detect a single *A. palmeri* seed in a pool of 199 *A. tuberculatus* seeds.

TABLE 9

Diagnostic criteria for all three markers.

| Marker # | True Positive | True Negative | PPV | NPV | Accuracy | F1 score |
|---|---|---|---|---|---|---|
| Marker 1 | 100% | 99.59% | 99.42% | 100% | 99.76% | 0.9971 |
| Marker 2 | 100% | 99.73% | 99.61% | 100% | 99.84% | 0.9981 |
| Marker 3 | 99.80% | 100% | 100% | 99.87% | 99.92% | 0.9991 |

PPV, positive predictor value;
NPV, negative predictor value.

Discussion
Marker Validation

The recent spread of *A. palmeri* from its native range and the fact it has been listed as a prohibited noxious weed species in several states has led to an increased demand for a non-morphological diagnostic assay that distinguishes *A. palmeri* from other *Amaranthus* species; however, this can be difficult due to the relatedness of common *Amaranthus* species, the lack of complete genetic information for these species, and the potential for samples to have hundreds of individuals in each testable DNA pool. Earlier methods based on restriction site polymorphisms in PCR-amplified internal transcribed spacer (ITS) regions have been useful for *Amaranthus* species identification but have only been validated against limited populations (*Pest Manage Sci* 73:2221-2224 (2017)). Recent developments in Omics provide a wealth of tools for the development of new markers (Patterson et al., 2019). These tools can be used to identify species diagnostic SNPs, which can then be genotyped through approaches such as KASP to provide a species identification (Patterson et al., 2017). We utilized this approach to develop a suite of three high precision KASP markers for identifying *A. palmeri* against non-*A. palmeri* species of the same genus. These markers meet or exceed the performance of any test commercially available at this time.

All three KASP markers were 99.75% accurate and therefore offer a reliable tool for *A. palmeri* identification. Minimizing false negative rates is a central goal for invasive species screening, a false negative represents an *A. palmeri* individual that was not identified as such and, thus, escapes control efforts. Individuals who possess the false negative SNP state may then spread this SNP from a newly invaded colony, which will undermine the reliability of *A. palmeri* screening over time. We address this risk in two ways: (1) we have developed markers targeting three different SNPs, and (2) our markers have extremely low false negative rates. Marker 1 demonstrated 99.76% accuracy, misidentifying only three individuals out of 1,248 total test samples. Markers 2 and 3 had similar results, with 99.84% and 99.92% accuracy, respectively. Critically, Markers 1 and 2 displayed a 0.00% false negative rate, correctly flagging all *A. palmeri* samples during testing. Marker 3 had a single *A. palmeri* individual that was not detected during testing. This individual was, however, correctly identified by the other two markers. The performance of Marker 3 was still exceptional, displaying a single undesirable call out of 1,253 individuals.

The other parameter of concern is the false positive rate. In our situation, a false positive represents a waste of resources being expended on the control of non-*A. palmeri* individuals. KASP Marker 1 demonstrated a false positive rate of 0.41%, which was driven only by three erroneous calls out of all individuals screened. We had a positive predictor value (PPV) of 99.29%, indicating that an assay result of *A. palmeri* corresponded with an actual *A. palmeri* individual in nearly all cases. Similar results were found with the other two markers, with 0.27% false positive rate (PPV 99.61%) and 0% false positive rate (PPV 100%) for Markers 2 and 3, respectively. These results indicate that for individual samples found in the field our assay performs exceptionally well and will be a valuable tool for accurately identifying targets for control efforts.

Detection Threshold

Prevention of *A. palmeri* establishment requires early identification and targeting the sources of propagule pressure. One of the major pathways of *A. palmeri* introduction is through contaminated seed lots. This has led to the listing of *A. palmeri* on prohibited noxious seed lists of several states, such as Iowa, Ohio, Minnesota, and South Dakota. Due to the difficulties in identifying *Amaranthus* seed morphologically, there has been a rapid adoption of genetic testing to identify *A. palmeri* contamination in pools of seed. Genetic testing is specifically required by some states before a sample can be certified as free from *A. palmeri* (Minnesota Department of Agriculture, 2020). This has created a large demand for high throughput bulk testing methods to identify *A. palmeri* seed in seed mixes. The sensitivity of a genetic test determines the maximum number of seeds that can be processed as a single sample, as well as the strength of separation between contaminated and non-contaminated samples. All three of our markers demonstrate extremely high sensitivity for detection of *A. palmeri* seed in mixed seed samples, and are able to reliably detect a single *A. palmeri* seed when extracted alongside 199 *A. tuberculatus* seeds (p<0.0001 for all three markers)(FIGS. 3-4). This detection level is the highest among any currently existing seed testing assays commercially available.

The reliability of any seed identification assay depends on the proper preparation of DNA being subjected to testing. Although DNA extraction of individual samples is quite straightforward, tissue disruption of pools of multiple *Amaranthus* seed poses more of a challenge. The small size of the seeds (~0.8-1.1 mm) and large number of seed in the testing pool can make it difficult to ensure that all samples are properly ground and lysed. Careful choice of disruption tube and grinding beads is recommended, as is the use of either liquid nitrogen or an overnight incubation in lysis buffer. Extended disruption times, as much as 8 minutes in total, may be necessary to disrupt all of the *Amaranthus* seeds in a sample. Visual inspection of the disrupted sample is recommended before proceeding with DNA extraction. Our protocols sufficiently addressed this challenge, demonstrated by our successful extraction of DNA from a single *A. palmeri* seed in a pool of 200 total seeds.

In addition to individual *A. palmeri* identification and bulk seed testing, our test also provides a utility to detect hybrids of *A. palmeri* and other *Amaranthus* species. A combination of *A. palmeri* and non-*A. palmeri* DNA will produce intermediate data points (FIG. 2). Hybridization is known to occur within the *Amaranthus* genus, particularly between *A. palmeri* and *A. spinosis* (Ward et al., 2013). Hybridization between *A. tuberculatus* and *A. hybridus* has also been confirmed (Trucco et al., 2005) although it may be unidirectional (Trucco et al., 2009). The hybridization potential of Amaranths has long been a concern for control efforts due to the number of herbicide resistance traits found in the weedy species. An *A. spinosis*×*A. palmeri* hybrid with resistance to multiple ALS-inhibitor herbicides was confirmed in Mississippi in 2016 (Molin et al., 2016). The spread of glyophsate resistance through hybrid formation has also been confirmed in a *A. spinosus*×*A. palmeri* hybrid in Mississippi (Nandula et al., 2014). Hybridization rates between Amaranths vary by species, but field values have been observed as high as 0.4% for *A. spinosus*×*A. palmeri* hybrids (Gaines et al., 2012). Our tests are based on three SNPs, which have a different homozygous state in *A. palmeri* and non-*A. palmeri* species, which gives our test the ability to identify *A. palmeri* hybrids with any other *Amaranthus* species. Compared to existing commercialized assays, our new tests offer a number of advantages: (1) we target novel SNPs which have been filtered to be *A. palmeri* specific from a GBS dataset of 817 accessions, (2) our assays have been validated against the most robust and diverse panel of *Amaranthus* accessions to date, including populations from South America and Africa, (3) by using KASP we avoid the need to normalize results against housekeeping genes, and (4) our assay is less sensitive to DNA concentration, making normalization steps easier. These traits make our assay easier to implement for smaller start-up labs, while continuing to provide high accuracy reliable results. It also opens up the opportunity for making use of these markers on field deployable hardware.

This work provides a framework for detecting rare variants and/or alleles in mixed pools of nucleic acids. This work innovated in two key was: (1) used a trans-species GBS approach to identify candidate diagnostic SNPs and (2) developed a robust statistical frame work for using KASP in situations where there are more than three genotyping states (instead of homozygous A, heterozygous, or homozygous B, our assay detects a continuous distribution of mixed pools of alleles). Theoretically, this technique could be used in several unique ways. For instance, determining the relative contribution of paralogues from different sub-genomes of a polyploid to a transcript pool, finding rare alleles in populations of mitochondria or chloroplasts, resolving different contributions of expression from different genes of closely related gene families, or measuring the abundance of a single species from a mixed microbe community of closely related species.

REFERENCES

Bolger, A. M., Lohse, M., Usadel, B., 2014. Trimmomatic: A flexible trimmer for Illumina sequence data. Bioinformatics 30, 2114-2120. https://doi.org/10.1093/bioinformatics/btu170

Chahal, P. S., Ganie, Z. A., Jhala, A. J., 2018. Overlapping Residual Herbicides for Control of Photosystem (PS) II- and 4-Hydroxyphenylpyruvate Dioxygenase (HPPD)-Inhibitor-Resistant Palmer amaranth (*Amaranthus palmeri* S. Watson) in Glyphosate-Resistant Maize. Front. Plant Sci. 8, 1-11. https://doi.org/10.3389/fpls.2017.02231

Culpepper, A. S., Grey, T. L., Vencill, W. K., Kichler, J. M., Webster, T. M., Brown, S. M., York, A. C., Davis, J. W., Hanna, W. W., 2006. Glyphosate-resistant Palmer amaranth (*Amaranthus palmeri*) confirmed in Georgia. Weed Sci. 54, 620-626. https://doi.org/10.1614/WS-06-001R.1

Danecek, P., Auton, A., Abecasis, G., Albers, C. A., Banks, E., DePristo, M. A., Handsaker, R. E., Lunter, G., Marth, G. T., Sherry, S. T., McVean, G., Durbin, R., 2011. The variant call format and VCFtools. Bioinformatics 27, 2156-2158. https://doi.org/10.1093/bioinformatics/btr330

Ertiro, B. T., Ogugo, V., Worku, M., Das, B., Olsen, M., Labuschagne, M., Semagn, K., 2015. Comparison of Kompetitive Allele Specific PCR (KASP) and genotyping by sequencing (GBS) for quality control analysis in maize. BMC Genomics 16, 1-12. https://doi.org/10.1186/s12864-015-2180-2

Gaines, T. A., Ward, S. M., Bukun, B., Preston, C., Leach, J. E., Westra, P., 2012. Interspecific hybridization transfers a previously unknown glyphosate resistance mechanism in *Amaranthus* species. Evol. Appl. 5, 29-38. https://doi.org/10.1111/j.1752-4571.2011.00204.x Gaines, T. A., Zhang, W., Wang, D., Bukun, B., Chisholm, S. T., Shaner, D. L., Nissen, S. J., Patzoldt, W. L., Tranel, P. J., Culpepper, A. S., Grey, T. L., Webster, T. M., Vencill, W. K., Sammons, R. D., Jiang, J., Preston, C., Leach, J. E., Westra, P., 2010. Gene amplification confers glyphosate resistance in *Amaranthus palmeri*. Proc. Natl. Acad. Sci. 107, 1029-1034. https://doi.org/10.1073/pnas.0906649107

Garrison, E., Marth, G., 2012. Haplotype-based variant detection from short-read sequencing 1-9.

Heap, I., 2019. The International Survey of Herbicide Resistant Weeds [WWW Document]. URL http://www.weedscience.org (accessed 8.19.19).

Jhala, A. J., Sandell, L. D., Rana, N., Kruger, G. R., Knezevic, S. Z., 2014. Confirmation and Control of Triazine and 4-Hydroxyphenylpyruvate Dioxygenase-Inhibiting Herbicide-Resistant Palmer Amaranth (*Amaranthus palmeri*) in Nebraska. Weed Technol. 28, 28-38. https://doi.org/10.1614/wt-d-13-00090.1

Klingaman, T., Oliver, L., 1994. Palmer Amaranth (*Amaranthus palmeri*) Interference in Soybeans (*Glycine max*). Weed Sci. 42, 523-527.

Kohrt, J. R., Sprague, C. L., Nadakuduti, S. S., Douches, D., 2017. Confirmation of a three-way (glyphosate, als, and atrazine)herbicide-resistant population of palmer amaranth (*Amaranthus palmeri*) in Michigan. Weed Sci. 65, 327-338. https://doi.org/10.1017/wsc.2017.2

Küpper, A., Borgato, E. A., Patterson, E. L., Netto, A. G., Nicolai, M., Carvalho, S. J. P., Nissen, S. J., Gaines, T. A., Christoffoleti, P. J., 2017. Multiple resistance to glyphosate and acetolactate synthase inhibitors in palmer amaranth (*Amaranthus palmeri*) identified in Brazil. Weed Sci. 65, 317-326. https://doi.org/10.1017/wsc.2017.1

Li, H., Durbin, R., 2009. Fast and accurate short read alignment with Burrows-Wheeler transform. Bioinformatics 25, 1754-1760. https://doi.org/10.1093/bioinformatics/btp324

Massinga, R. A., Currie, R. S., Horak, M. J., Boyer, J., 2001. Interference of Palmer Amaranth in Corn. Source Weed Sci. Weed Sci. 49, 202-208. https://doi.org/10.1614/0043-1745(2001)049 [0202:IOPAIC]2.0.CO;2

Minnesota Department of Agriculture, 2020. Palmer Amaranth in Minnesota [WWW Document]. URL https:// www.mda.state.mn.us/plants-insects/palmer-amaranth-minnesota (accessed 2.3.20).

Molin, W. T., Nandula, V. K., Wright, A. A., Bond, J. A., 2016. Transfer and Expression of ALS Inhibitor Resistance from Palmer Amaranth (*Amaranthus palmeri*) to an *A. spinosus×A. palmeri* Hybrid. Weed Sci. 64, 240-247. https://doi.org/10.1614/ws-d-15-00172.1

Morgan, G. D., Baumann, P. A., Chandler, J. M., 2001. Competitive Impact of Palmer Amaranth (*Amaranthus palmeri*) on Cotton (*Gossypium hirsutum*) Development and Yield 1. Weed Technol. 15, 408-412. https://doi.org/10.1614/0890-037x(2001)015[0408:ciopaa]2.0.co;2

Murphy, B. P., Plewa, D. E., Phillippi, E., Bissonnette, S. M., Tranel, P. J., 2017. A quantitative assay for *Amaranthus palmeri* identification. Pest Manag. Sci. 73, 2221-2224. https://doi.org/10.1002/ps.4632

Nakka, S., Godar, A. S., Thompson, C. R., Peterson, D. E., Jugulam, M., 2017a. Rapid detoxification via glutathione S-transferase (GST) conjugation confers a high level of atrazine resistance in Palmer amaranth (*Amaranthus palmeri*). Pest Manag. Sci. 73, 2236-2243. https://doi.org/10.1002/ps.4615

Nakka, S., Thompson, C. R., Peterson, D. E., Jugulam, M., 2017b. Target Site—Based and Non—Target Site Based Resistance to ALS Inhibitors in Palmer Amaranth (*Amaranthus palmeri*). Weed Sci. 65, 681-689. https://doi.org/10.1017/wsc.2017.43

Nandula, V. K., Wright, A. A., Bond, J. A., Ray, J. D., Eubank, T. W., Molin, W. T., 2014. EPSPS amplification in glyphosate-resistant spiny amaranth (*Amaranthus spinosus*): A case of gene transfer via interspecific hybridization from glyphosate-resistant Palmer amaranth (*Amaranthus palmeri*). Pest Manag. Sci. 70, 1902-1909. https://doi.org/10.1002/ps.3754

Oliveira, M. C., Gaines, T. A., Patterson, E. L., Jhala, A. J., Irmak, S., Amundsen, K., Knezevic, S. Z., 2018. Interspecific and intraspecific transference of metabolism-based mesotrione resistance in dioecious weedy *Amaranthus*. Plant J. 96, 1051-1063. https://doi.org/10.1111/tpj.14089

Patterson, E. L., Flemin, M. B., Kessler, K. C., Nissen, S. J., Gaines, T. A., 2017. A KASP genotyping method to identify northern watermilfoil, Eurasian watermilfoil, and their interspecific hybrids. Front. Plant Sci. 8, 1-10. https://doi.org/10.3389/fpls.2017.00752

Patterson, E. L., Saski, C., Kupper, A., Beffa, R., Gaines, T. A., 2019. Omics Potential in Herbicide-Resistant Weed Management. Plants 8, 1-14.

Peterson, D. E., Nakka, S., Jugulam, M., Thompson, C. R., Godar, A. S., 2017. Rapid detoxification via glutathione S-transferase (GST) conjugation confers a high level of atrazine resistance in Palmer amaranth (*Amaranthus palmeri*). Pest Manag. Sci. 73, 2236-2243. https://doi.org/10.1002/ps.4615

Ravet, K., Patterson, E. L., Krahmer, H., Hamouzova, K., Fan, L., Jasieniuk, M., Lawton-Rauh, A., Malone, J. M., McElroy, J. S., Merotto, A., Westra, P., Preston, C., Vila-Aiub, M. M., Busi, R., Tranel, P. J., Reinhardt, C., Saski, C., Beffa, R., Neve, P., Gaines, T. A., 2018. The power and potential of genomics in weed biology and management. Pest Manag. Sci. 74, 2216-2225. https://doi.org/10.1002/ps.5048

Salas-Perez, R. A., Burgos, N. R., Rangani, G., Singh, S., Refatti, J. P., Piveta, L., Tranel, P. J., Mauromoustakos, A., Scott, R. C., 2017. Frequency of Gly-210 Deletion Mutation among Protoporphyrinogen Oxidase Inhibitor-Resistant Palmer Amaranth (*Amaranthus palmeri*) Populations. Weed Sci. 65, 718-731. https://doi.org/10.1017/wsc.2017.41

Salas, R. A., Burgos, N. R., Tranel, P. J., Singh, S., Glasgow, L., Scott, R. C., Nichols, R. L., 2016. Resistance to PPO-inhibiting herbicide in Palmer amaranth from Arkansas. Pest Manag. Sci. 72, 864-869. https://doi.org/10.1002/ps.4241

Schwartz-Lazaro, L. M., Norsworthy, J. K., Scott, R. C., Barber, L. T., 2017. Resistance of two Arkansas Palmer amaranth populations to multiple herbicide sites of action. Crop Prot. 96, 158-163. https://doi.org/10.1016/j.cropro.2017.02.022

Sosnoskie, L. M., Webster, T. M., Kichler, J. M., MacRae, A. W., Grey, T. L., Culpepper, A. S., 2012. Pollen-Mediated Dispersal of Glyphosate-Resistance in Palmer Amaranth under Field Conditions. Weed Sci. 60, 366-373. https://doi.org/10.1614/WS-D-11-00151.1

Steckel, L. E., Sprague, C. L., Stoller, E. W., Wax, L. M., 2004. Temperature effects on germination of nine *Amaranthus* species. Weed Sci. 52, 217-221. https://doi.org/10.1614/WS-03-012R Trucco, F., Jeschke, M. R., Rayburn, A. L., Tranel, P. J., 2005. *Amaranthus hybridus* can be pollinated frequently by *A. tuberculatus* under field conditions. Heredity (Edinb). 94, 64-70. https://doi.org/10.1038/sj.hdy.6800563

Trucco, F., Tatum, T., Rayburn, A. L., Tranel, P. J., 2009. Out of the swamp: Unidirectional hybridization with weedy species may explain the prevalence of *Amaranthus tuberculatus* as a weed. New Phytol. 184, 819-827. https://doi.org/10.1111/j.1469-8137.2009.02979.x Varanasi, V. K., Brabham, C., Norsworthy, J. K., 2018. Confirmation and Characterization of Non—target site Resistance to Fomesafen in Palmer amaranth (*Amaranthus palmeri*). Weed Sci. 66, 702-709. https://doi.org/10.1017/wsc.2018.60

Ward, S. M., Webster, T. M., Steckel, L. E., 2013. Palmer Amaranth (*Amaranthus palmeri*): A Review. Weed Technol. 27, 12-27. https://doi.org/10.1614/wt-d-12-00113.1

What is claimed:

1. A method for determining whether a sample contains *Amaranthus palmeri* plant material, the method comprising:
   a. providing a primer set comprising:
      i. a first primer that recognizes a first locus in the genome of *Amaranthus* and is specific to the sequence variant found in *Amaranthus palmeri*,
      ii. a second primer that recognizes the first locus in the genome of *Amaranthus* and is specific to the sequence variant found in all *Amaranthus* species other than *Amaranthus palmeri*, and
      iii. a third primer that recognizes a second locus in the genome of *Amaranthus* and is specific to a sequence found in all *Amaranthus* species,
      wherein the first primer comprises SEQ ID NO: 1 and the second primer comprises SEQ ID NO: 2 or the first primer comprises SEQ ID NO: 4 and the second primer comprises SEQ ID NO: 5;
   b. obtaining a sample comprising DNA derived from at least one *Amaranthus* plant;
   c. forming a reaction mixture by contacting the primer set with the sample under conditions in which the first primer and second primer each form a primer pair with the third primer, such that the primer pairs bind to and amplify nucleotide sequences in the sample that are recognized by the primer pairs;
   d. amplifying DNA in the sample, wherein any DNA amplified using the first primer forms a first amplification product and any DNA amplified using the second primer forms a second amplification product;
   e. detecting whether the first amplification product is present following amplification, wherein the presence of the first amplification product indicates that the sample contains *Amaranthus palmeri* plant material.

2. The method of claim 1, further comprising quantifying the first amplification product and the second amplification product to calculate the abundance of *Amaranthus palmeri* DNA relative to total *Amaranthus* DNA in the sample.

3. The method of claim 1, wherein the sample comprises DNA from a plurality of *Amaranthus* plants.

4. The method of claim 3, wherein the sample comprises DNA from more than five *Amaranthus* plants.

5. A method for genotyping a *Amaranthus* plant by performing the method of claim 1 using a sample comprising DNA from a single *Amaranthus* plant and then further detecting whether the second amplification product is present following amplification, wherein:
   a. the presence of only the first amplification product indicates that the plant is *Amaranthus palmeri*;
   b. the presence of only the second amplification product indicates that the plant is an *Amaranthus* species other than *Amaranthus palmeri*; and
   c. the presence of both the first amplification product and the second amplification product indicates the plant is a hybrid of *Amaranthus palmeri* and another *Amaranthus* species.

6. The method of claim 1, wherein:
   the first primer further comprises a first reporter sequence and the second primer further comprises a second reporter sequence;
   the reaction mixture of step (c) further comprises a first reporter molecule that binds to the first reporter sequence in the first amplification product and a second reporter molecule that binds to the second reporter sequence in the second amplification product; and
   binding of the first reporter molecule produces a first detectable signal and binding of the second reporter molecule produces a second detectable signal in step (d).

7. The method of claim 6, wherein the first detectable signal is produced by a FAM fluorophore and the second detectable signal is produced by a HEX fluorophore.

8. The method of claim 1, wherein the method is performed using a first primer set on a first portion of the sample and a second primer set on a second portion of the sample, and wherein the first primer set and second primer set comprise different primers.

9. The method of claim 8, further comprising performing the method using a third primer set on a third portion of the sample, wherein each of the first primer set, the second primer set, and the third primer set comprise different primers.

10. The method of claim 8, wherein:
    a. in the first primer set, the first primer comprises SEQ ID NO: 1 and the second primer comprises SEQ ID NO: 2; and
    b. in the second primer set, the first primer comprises SEQ ID NO: 4 and the second primer comprises SEQ ID NO: 5.

11. The method of claim 8, wherein in the second primer set, the first primer comprises SEQ ID NO: 7 and the second primer comprises SEQ ID NO: 8.

12. The method of claim 9, wherein:
    a. in the first primer set, the first primer comprises SEQ ID NO: 1 and the second primer comprises SEQ ID NO: 2;
    b. in the second primer set, the first primer comprises SEQ ID NO: 4 and the second primer comprises SEQ ID NO: 5; and
    c. in the third primer set, the first primer comprises SEQ ID NO: 7 and the second primer comprises SEQ ID NO: 8.

13. The method of claim 1, wherein the primer sets are selected from:
    a. A primer set wherein the first primer comprises SEQ ID NO: 1, the second primer comprises SEQ ID NO: 2, and the third primer comprises SEQ ID NO: 3; and
    b. A primer set wherein the first primer comprises SEQ ID NO: 4, the second primer comprises SEQ ID NO: 5, and the third primer comprises SEQ ID NO: 6.

14. The method of claim 1, wherein the third primer has a $T_m$ that is within 5° C. of the $T_m$ of both the first primer and the second primer.

15. The method of claim 1, wherein the second locus recognized by the third primer is within 1000 bp of the first locus recognized by both the first primer and the second primer within the *Amaranthus* genome.

16. A kit for determining relative abundance of *Amaranthus palmeri* DNA in a sample, the kit comprising:
    a. a first primer that recognizes a first locus in the genome of *Amaranthus* and is specific to the sequence variant found in *Amaranthus palmeri*,
    b. a second primer that recognizes the first locus and is specific to the sequence variant found in all *Amaranthus* species other than *Amaranthus palmeri*, and
    c. a third primer that recognizes a second locus in the genome of *Amaranthus* and is specific to a sequence found in all *Amaranthus* species,
    d. a first heterologous reporter molecule, and
    e. a second heterologous reporter molecule,
    wherein the first primer comprises SEQ ID NO: 1 and the second primer comprises SEQ ID NO: 2 or the first primer comprises SEQ ID NO: 4 and the second primer comprises SEQ ID NO: 5; and wherein the first primer further comprises a first heterologous reporter sequence that is complementary in sequence to the first heterologous reporter molecule, and the second primer further comprises a second heterologous reporter sequence that is complementary in sequence to the second heterologous reporter molecule; and wherein the first heterologous reporter sequence comprises one of SEQ ID NO: 10 or SEQ ID NO: 11 and the second heterologous reporter sequence comprises the other of SEQ ID NO: 10 or SEQ ID NO: 11.

17. The kit of claim 16, wherein the first heterologous reporter molecule and second heterologous reporter molecule are supplied as FRET cassettes.

18. The kit of claim 16, further comprising a positive control for *Amaranthus palmeri* DNA and/or a positive control for DNA from all *Amaranthus* species other than *Amaranthus palmeri*.

* * * * *